US009310362B2

(12) United States Patent
Muraguchi et al.

(10) Patent No.: US 9,310,362 B2
(45) Date of Patent: Apr. 12, 2016

(54) MICROWELL ARRAY CHIP AND METHOD OF MANUFACTURING SAME

(75) Inventors: Atsushi Muraguchi, Toyama (JP); Hiroyuki Kishi, Toyoma (JP); Yoshiharu Tokimitsu, Toyama (JP); Sachiko Kondo, Toyama (JP); Tsutomu Obata, Takaoka (JP); Satoshi Fujiki, Takaoka (JP); Yoshiyuki Yokoyama, Takaoka (JP); Hirofumi Nabesawa, Takaoka (JP); Sotohiro Takabayashi, Takaoka (JP); Katsumi Tanino, Takaoka (JP)

(73) Assignee: VALNEVA, Lyons (FR)

( * ) Notice: Subject to any disclaimer, the term of this patent is extended or adjusted under 35 U.S.C. 154(b) by 0 days.

(21) Appl. No.: 13/088,582

(22) Filed: Apr. 18, 2011

(65) Prior Publication Data

US 2011/0195496 A1 Aug. 11, 2011

Related U.S. Application Data

(63) Continuation of application No. 10/573,289, filed as application No. PCT/JP2004/014285 on Sep. 22, 2004, now abandoned.

(30) Foreign Application Priority Data

Sep. 25, 2003 (JP) .................................. 2003-333363
Sep. 29, 2003 (JP) .................................. 2003-336771
Sep. 29, 2003 (JP) .................................. 2003-336793

(51) Int. Cl.
*C12N 5/16* (2006.01)
*C12N 5/00* (2006.01)
(Continued)

(52) U.S. Cl.
CPC ....... *G01N 33/54366* (2013.01); *B01J 19/0046* (2013.01); *A61K 35/12* (2013.01); *A61K 48/00* (2013.01); *B01J 2219/00659* (2013.01)

(58) Field of Classification Search
CPC ....... A61K 38/00; A61K 48/00; A61K 35/12; A01K 2217/05; C07K 2319/00; G01N 33/54366
USPC .................................... 435/287.1, 287.2, 325
See application file for complete search history.

(56) References Cited

U.S. PATENT DOCUMENTS 4,729,949 A 3/1988 Weinreb et al.
5,272,081 A 12/1993 Weinreb et al.
(Continued)

FOREIGN PATENT DOCUMENTS

EP 0 205 387 12/1986
EP 0258565 A2 3/1988
(Continued)

OTHER PUBLICATIONS

Rasmussen et al., Cell-Dependent Hapten-Specific and Polyclonal B Cell Response Require Release of Interleukin 5. The Journal of Immunology. vol. 140, No. 3, pp. 705-712. Feb. 1, 1988. The American Association of Immunologists.*

(Continued)

*Primary Examiner* — Michael Hobbs
(74) *Attorney, Agent, or Firm* — Birch, Stewart, Kolasch & Birch, LLP

(57) ABSTRACT

A microwell array chip made of silicon and having multiple microwells where each microwell is used to store a single specimen organic cell. The microwell of the array chip is of a size and shape to hold just one organic cell and the interior surface of the microwells are coated with a fluorocarbon film.

6 Claims, 16 Drawing Sheets

(51) Int. Cl.
*G01N 33/543* (2006.01)
*B01J 19/00* (2006.01)
*A61K 35/12* (2015.01)
*A61K 48/00* (2006.01)

(56) References Cited

U.S. PATENT DOCUMENTS

| | | | |
|---|---|---|---|
| 5,310,674 | A | 5/1994 | Weinreb et al. |
| 5,506,141 | A | 4/1996 | Weinreb et al. |
| 6,087,103 | A | 7/2000 | Burmer |
| 6,197,575 | B1 | 3/2001 | Griffith et al. |
| 6,210,910 | B1 | 4/2001 | Walt et al. |
| 6,232,066 | B1 | 5/2001 | Felder et al. |
| 6,377,721 | B1 | 4/2002 | Walt et al. |
| 6,410,252 | B1 | 6/2002 | Lehmann et al. |
| 6,548,263 | B1 | 4/2003 | Kapur et al. |
| 6,565,813 | B1 | 5/2003 | Garyantes |
| 2002/0001576 | A1* | 1/2002 | Sekine et al. ............ 424/93.7 |
| 2002/0072116 | A1 | 6/2002 | Bhatia et al. |
| 2003/0017349 | A1 | 1/2003 | Brown et al. |
| 2003/0027214 | A1 | 2/2003 | Kamb |
| 2003/0030184 | A1 | 2/2003 | Kim et al. |
| 2003/0032002 | A1 | 2/2003 | Wang et al. |
| 2003/0064386 | A1 | 4/2003 | Karaki et al. |
| 2003/0113833 | A1 | 6/2003 | Oka et al. |
| 2004/0191924 | A1 | 9/2004 | Hunter et al. |
| 2005/0112033 | A1 | 5/2005 | Zhang et al. |
| 2005/0220675 | A1 | 10/2005 | Reed et al. |
| 2006/0078946 | A1 | 4/2006 | Muraguchi et al. |
| 2006/0134704 | A1 | 6/2006 | Muraguchi et al. |
| 2009/0181859 | A1 | 7/2009 | Muraguchi et al. |

FOREIGN PATENT DOCUMENTS

| | | |
|---|---|---|
| JP | 59-31685 A | 2/1984 |
| JP | 63-106565 A | 5/1988 |
| JP | 5-240869 A | 9/1993 |
| JP | 2003-33177 A | 2/2003 |
| WO | WO 02/055653 A | 7/2002 |

OTHER PUBLICATIONS

Schilizzi et al. "Studies on the INduction of Antigen-Specific Antibody in Anti-CD40 Cultured Human B Lymphocytes" Develpomental Immunology 6: 261-271, 1998.*

Abts, H. et al, "CD20 positive human B lymphocytes separated with the magnetic cell sorter (MACS) can be induced to proliferation and antibody secretion in vitro," Journal of Immunological Methods, 1989, vol. 125, pp. 19-28.

Altman, J. D., et al., "Phenotypic Analysis of Antigen-Specific T Lymphocytes," Science, Oct. 4, 1996, vol. 274, pp. 95-96.

Canadian IP Office, Canada Office Action, Appl. No. 2,544,470, Jul. 20, 2010, pp. 1-4.

Chinese First Office Action, Appl. No. 200480034519.6, May 8, 2009, pp. 1-13.

EPO Supplementary European Search Report, Appl. No. 04773462.9, Jun. 12, 2007, pp. 1-3.

International Search Report, PCT/JP2004/014285, Mar. 29, 2005.

PCT International Preliminary Report on Patentability and Written Opinion of the International Search Authority, Appl. No. PCT/JP2004/014285, Jun. 20, 2006, pp. 1-5.

USPTO Office Action, U.S. Appl. No. 10/573,289, Aug. 5, 2009, pp. 1-9.

USPTO Office Action, U.S. Appl. No. 10/573,289, Jan. 19, 2011, pp. 1-12, Inventor: Maraguchi et al.

USPTO Office Action, U.S. Appl. No. 10/573,289, Mar. 11, 2010, pp. 1-11, Inventor: Maraguchi et al.

USPTO Office Action, U.S. Appl. No. 10/573,289, May 17, 2010, pp. 1-3, Inventor: Maraguchi et al.

USPTO Office Action, U.S. Appl. No. 10/573,289, Sep. 10, 2010, pp. 1-13, Inventor: Maraguchi et al.

Yamamura, S., et al, "Single-Cell Microarray for Analyzing Cellular Response," Anal. Chem., 2005, vol. 77, pp. 8050-8056.

Abbas et al., "Cellular and Molecular Immunology", Cellular and Molecular Immunology 2nd Edition, W.B. Saunders Company, Philadelphia, Pennsylvania, 1994, pp. 90-93.

Chen et al., "A novel micro-well array chip for liquid phase biomaterial processing and detection", Sensors and Actuators A, vol. 108, 2003, pp. 193-200.

Clark et al., "Regulation of Human B-Cell Activation and Adhesion", Annu. Rev. Immunol, vol. 9, 1991, pp. 97-127.

Ostuni et al., "Selective Deposition of Proteins and Cells in Arrays of Microwells", Langmuir, vol. 17, 2001 (Published online Apr. 5, 2001), pp. 2828-2834.

Sredni et al., "Antigen-Specific, Proliferating T Lymphocyte Clones, Methodology, Specificity, MHC Restriction and Alloreactivity", Immunological Rev. vol. 54, 1981, pp. 187-206, Copenhagen, Denmark.

Steenbakkers et al., "A new approach to the generation of human or murine antibody producing hybridomas", Journal of Immunological Methods, vol. 152, 1992, pp. 69-77.

Ishida et al., "Methods of Conducting Immunological Experiments I, II", published by Nankodo (1995) pp. 742-747 (with Statement of Relevancy).

Yano et al., "Lymphocyte Function Detection Methods", Chugai Igaku Corp., (1994) pp. 262-267 (with Statement of Relevancy).

* cited by examiner

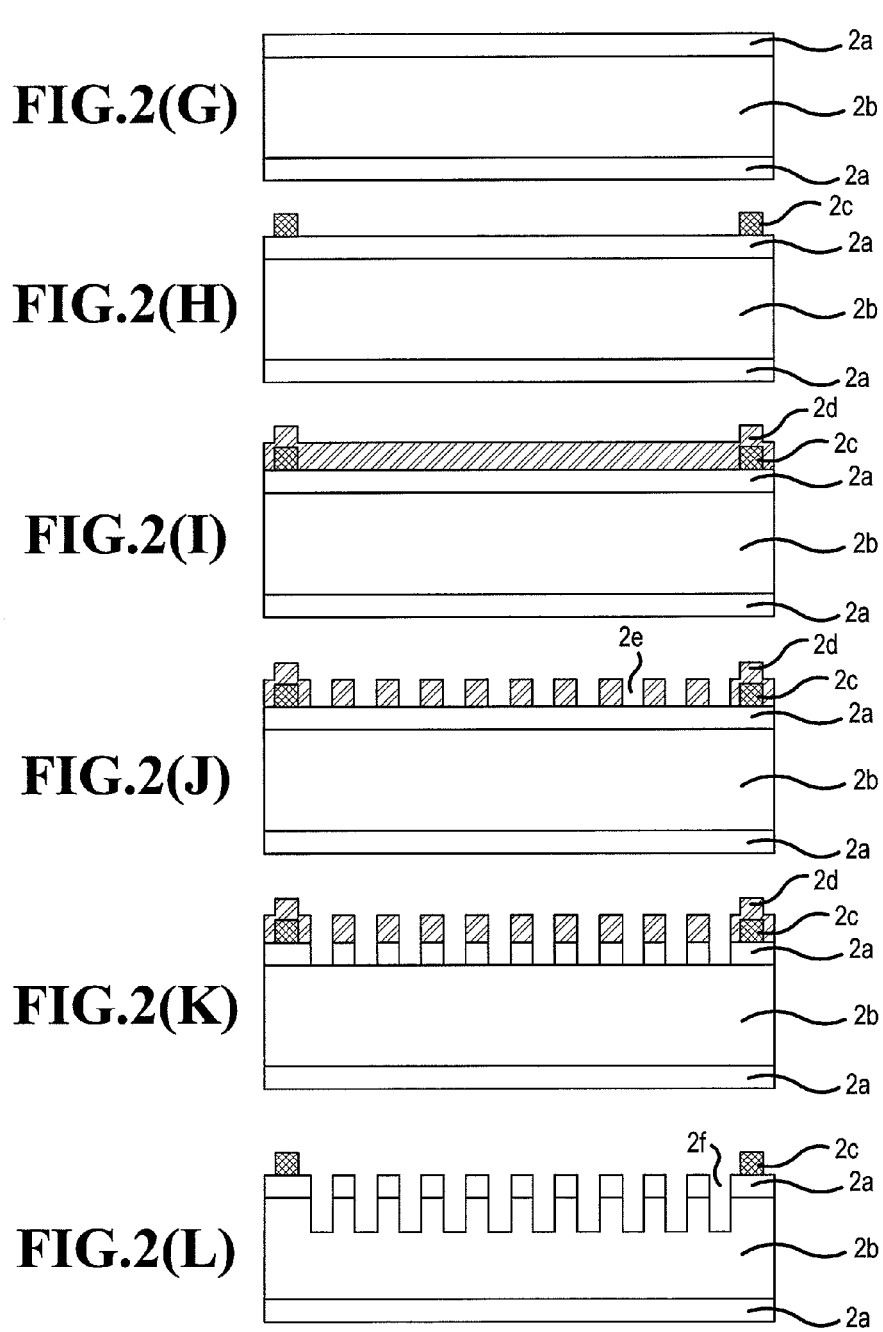

__US 9,310,362 B2__

MICROWELL ARRAY CHIP AND METHOD OF MANUFACTURING SAME

This application is a Continuation of and claims the benefit of co-pending U.S. application Ser. No. 10/573,289, filed Feb. 20, 2007 now abandoned, which is the national stage of PCT Application No. PCT/JP2004/014285 filed on Sep. 22, 2004. Benefit of priority is also claimed to JP 2003-333363 filed on Sep. 25, 2003, JP 2003-336771 filed on Sep. 29, 2003 and JP 2003-336793 filed Sep. 29, 2003. The entire contents of each of the above documents is hereby incorporated by reference.

TECHNICAL FIELD

Aspect I of the present invention relates to a microwell array chip that can be used to detect organic cells such as antigen-specific lymphocytes. In particular, Aspect I of the present invention relates to a microwell array chip in which the position of a given microwell is readily determined.

Aspect II of the present invention relates to a microwell array chip, and a method for manufacturing the same, having good collection efficiency of organic cells in and recovery efficiency of organic cells from microwells.

Aspect III of the present invention relates to a microwell array chip made of silicon that can be used to detect organic cells such as antigen-specific lymphocytes. In particular, Aspect III of the present invention relates to a microwell array chip in which organic cells stored in microwells can be readily recovered as needed.

BACKGROUND ART

Conventionally, antigen-specific lymphocytes have been detected by adding about 200,000 lymphocytes to each well of a 96-well plate and culturing the lymphocytes in the presence of antigen for from three days to a week (Methods of Detecting Lymphocyte Functions", Junichi YANO, Michio FUJIWARA, eds., Chugai Igakusha (1994), "Methods of Conducting Immunity Experiments I, II", Shunsuke ISHIDA, Susumu KONDA, Morosuke MOTO, Toshiyuki HAMAOHKA, eds., Nankodo (1995)). This method makes it possible to determine that an antigen-specific lymphocyte is present within a group of about 200,000 lymphocytes. However, it does not permit the identification of individual antigen-specific lymphocytes present within the group of lymphocytes.

By contrast, a method has been developed and put into practice in recent years in which fluorescent pigment-labeled antigen molecules are mixed with lymphocytes to cause the fluorescently labeled antigen to bind to antigen receptors on the antigen-specific lymphocytes, and the lymphocytes that have bound the fluorescently labeled antigen are detected with a flow cytometer (Altman J. D., Moss P. A., Goulder P. J., Barouch D. H., McHeyzer-Williams M. G., Bell J. I., McMichael A. J., Davis M. M. Phenotype analysis of antigen-specific T lymphocytes, Science, 274: 94-96, 1996). In this method, a single lymphocyte that has bound an antigen can be identified. Further, it is also possible to separate out a single lymphocyte that has bound an antigen.

However, the above detection method requires an expensive and complex device known as a cell sorter for separation. In addition, it presents the following problems:

(1) It is difficult to set the conditions in the device for separation; great skill is required to operate the device and separate cells;

(2) Due to high background noise, when the frequency of the antigen-specific lymphocyte is 0.1 percent or less, the antigen-specific lymphocyte cannot be detected;

(3) Cell separation efficiency is low;

(4) Time is required to separate low frequency cells; and (5) Although the binding of antigen can be confirmed, the reaction by which the lymphocyte binds the antigen cannot be analyzed.

Another method of detecting antigen-specific lymphocytes has been developed in which antigen molecules bound to magnetic beads are mixed with lymphocytes to cause the magnetic bead-bound antigen to bind to the antigen receptors of the antigen-specific lymphocytes, and a magnet is used to separate the antigen-specific lymphocytes (Abts H., Emmerich M., Miltenyi S., Radbruch A., Tesch H., CD20 positive human B lymphocytes separated with the magnetic sorter (MACS) can be induced to proliferation and antibody secretion in vitro. Journal of Immunological Methods 125:19-28, 1989).

In this method, no complex device is required, cells are rapidly separated, and the binding of antigen can be confirmed. However, how the lymphocytes that have bound the antigen have reacted with the antigen (intracellular signal transmission, RNA synthesis, protein synthesis, or some other metabolic physiological reaction of the cell) cannot be analyzed. Further, antigen-specific lymphocytes with a frequency of 0.1 or less cannot be detected.

By contrast, the present inventors conducted various investigations into providing a method for detecting antigen-specific lymphocytes that does not require a complex device, separates cells rapidly, can confirm the binding of antigen, can detect antigen-specific lymphocytes of low frequency (0.001 percent or more), permits analysis of how the lymphocyte that has bound an antigen reacts with the antigen, and permits separation of antigen-specific lymphocytes. The present inventors also developed a method of detecting the antigen specificity of individual lymphocytes and recovering antigen-specific lymphocytes that are detected.

However, no microwell array chip was known that could separately detect the antigen specificity of individual lymphocytes and permit recovery of the antigen-specific lymphocytes that were detected.

Accordingly, the present inventors conducted extensive research into providing a microwell array chip that could be used in the above-described detection method and that could hold a single lymphocyte in a single microwell. The present inventors fabricated test microwell array chips in which microwells of roughly a size capable of containing a single lymphocyte were formed on a substrate surface, and conducted tests in which lymphocytes were stored (collected) in microwells and recovered from microwells. In this process, the present inventors determined that when recovering antigen-specific lymphocytes detected in an array chip in which multiple minute microwells had been provided, and in particular, when conducting detection and recovery in separate steps, the reliable recovery of antigen-specific lymphocytes without error from the microwells in which they had been detected required reliable determination of the positions of the microwells. That is, in array chips in which multiple microwells are simply arrayed, there is a problem in that it is difficult to readily determine the position of a specific microwell.

In the above process, the present inventors further determined that when the array chip was washed after collecting the lymphocytes in the microwells using a cell suspension in the course of storing lymphocytes in microwells, there was a problem in that a large number of cells ended up flowing out of the microwells, causing the collection efficiency and filling rate to decrease markedly.

Accordingly, the first object of the present invention is to provide a microwell array chip lending itself to use in the above-described detection method and permitting the storage of single lymphocytes in single microwells. In particular, Aspect I of the present invention has for its object to provide a microwell array chip permitting the ready determination of the positions of multiple minute microwells.

The second object of the present invention is to provide a microwell array chip in which cells such as lymphocytes that have been collected in microwells tend not to flow out of the microwells during subsequent washing.

The third object of the present invention is to provide a microwell array chip lending itself to use in the above-described detection method and capable of storing individual lymphocytes in individual microwells.

In particular, Aspect III of the present invention has for its object to provide a microwell array chip permitting the ready recovery of a single lymphocyte stored in a microwell. Aspect III of the present invention has the further object of providing a microwell array chip that is not limited to lymphocytes, but permits the storage of a single organic cell in a single microwell.

BRIEF DESCRIPTION OF THE INVENTION

To achieve the above-stated first object, Aspect I of the present invention is as follows.

(1) A microwell array chip in which multiple microwells are present on a principal surface of a substrate, said microwells being of a shape and size permitting the storage of only a single organic cell in each microwell,
wherein microwell markers are present on the same substrate surface as the openings of the microwells.

(2) The microwell array chip according to (1) wherein said multiple microwells are arranged horizontally and vertically at identical spacing and markers are provided at a prescribed number of microwells.

(3) The microwell array chip according to (1) or (2) wherein said multiple microwells are positioned on a principal surface of said substrate by being divided into groups each comprising a prescribed number of microwells and markers are provided in a manner permitting determination of the position of each group.

(4) The microwell array chip according to (3) wherein the number of microwells in each group falls within a range of from 10 to 10,000.

(5) The microwell array chip according to any of (1) to (4) wherein said marker is comprised of a fluorescent material or a reflective material.

(6) The microwell array chip according to any of (1) to (5) wherein said marker is a positioning marker.

(7) The microwell array chip according to any of (1) to (6) wherein said substrate is made of silicon, metal, or resin.

(8) The microwell array chip according to any of (1) to (7) wherein the shape of said microwells is cylindrical, polyhedral comprised of multiple surfaces, inversely conical, inversely pyramidal, or a combination of two or more of the above.

(9) The microwell array chip according to any of (1) to (8) wherein the diameter of the largest circle that can be inscribed within the planar shape of the microwells falls within a range of from 0.5 to 2-fold the diameter of the organic cell that is to be contained in the microwells, and the depth of the microwells falls within a range of from 0.5 to 4-fold the diameter of the organic cell that is to be contained in the microwells.

(10) The microwell array chip according to any of (1) to (9) wherein the organic cell is a lymphocyte and the microwell array chip is employed to detect single antigen-specific lymphocytes.

(11) The microwell array chip according to any of (1) to (10) wherein a hydrophobic region is provided in a manner surrounding said multiple microwells on said principal surface.

(12) The microwell array chip according to (11) wherein said hydrophobic region is comprised of a silicon surface or fluorine-containing surface.

To achieve the above-stated second object, Aspect II of the present invention is as follows.

(13) A microwell array chip having multiple microwells on a principal surface of a substrate, said microwells being of a shape and size permitting the storage of only a single organic cell in each microwell,
wherein protrusions are present in the openings of said microwells so as to narrow said openings.

(14) The microwell array chip according to (13) wherein said protrusions are formed by providing a film on the substrate surface that protrudes into the openings.

(15) The microwell array chip according to (13) or (14) wherein the size of the openings formed by said protrusions permits the passage of the organic cell to be stored in the microwell.

(16) The microwell array chip according to any of (13) to (15) wherein said substrate is made of silicon, metal, or resin.

(17) The microwell array chip according to any of (14) to (16) wherein the film provided on said substrate surface is an oxide film, nitride film, impurity diffusion film, metal film, or resin film.

(18) A method for manufacturing the microwell array chip according to (13) comprising the steps of:
forming a film on at least one principal surface of a substrate;
applying a resist coating on the film that has been formed;
exposing the resist surface through a mask having a microwell pattern and removing uncured portions of resist;
etching the exposed portions of said film and substrate to fabricate wells in the form of a microwell array; and
removing the resist.

(19) The method for manufacturing a microwell array chip according to (18) wherein said substrate is made of silicon, metal, or resin.

(20) The method for manufacturing a microwell array chip according to (18) or (19) wherein said film provided on said substrate surface is an oxide film, nitride film, impurity diffusion film, metal film, or resin film.

(21) The microwell array chip according to any of (13) to (20) wherein a hydrophobic region is provided in a manner surrounding said multiple microwells on said principal surface.

(22) The microwell array chip of (21) wherein said hydrophobic region has a silicon surface or fluorine-containing surface.

To achieve the above-stated third object, Aspect III of the present invention is as follows.

(23) A microwell array chip made of silicon and having multiple microwells, each microwell being used to store a single specimen organic cell,
wherein each microwell is of a size and shape holding just one organic cell.

(24) The microwell array chip according to (23) wherein each of said microwells is cylindrical, polyhedral comprised of multiple surfaces, inversely conical, inversely pyramidal, or a combination of two or more of the above.

(25) The microwell array chip according to (23) or (24) wherein the diameter of the largest circle that can be inscribed within the planar shape of the microwells falls within a range of from 0.5 to 2-fold the diameter of the organic cell that is to be contained in the microwells, and the depth of the microwells falls within a range of from 0.5 to 4-fold the diameter of the organic cell that is to be contained in the microwells.

(26) The microwell array chip according to any of (23) to (25) wherein said organic cell is a lymphocyte and the microwell array chip is used to detect single antigen-specific lymphocytes.

(27) The microwell array chip according to any of (23) to (26) wherein the interior surface of said microwells is coated with a fluorocarbon film or a silicon oxide film.

(28) The microwell array chip according to (27) employed so that a single organic cell stored in a single microwell is recovered from the microwell.

(29) The microwell array chip according to any of (23) to (28) wherein a hydrophobic region is provided in a manner surrounding said multiple microwells on said principal surface.

(30) The microwell array chip according to (29) wherein said hydrophobic region has a silicon surface or fluorine-containing surface.

(31) A microwell array chip having a microwell on a principal surface of a substrate, wherein a hydrophobic surface region is provided in a manner surrounding said microwell on said principal surface.

(32) The microwell array chip according to (31) wherein said hydrophobic region has a silicon surface or fluorine surface.

BEST MODES OF IMPLEMENTING THE INVENTION

Aspect 1

Aspect 1 of the present invention is described below.
Microwell Array Chip

The microwell array chip of Aspect 1 of the present invention has multiple microwells on a principal surface of a substrate. The microwells are of a size and shape capable of storing just one organic cell per microwell. The microwell array chip of the present invention also has microwell markers on the same substrate surface as the microwell openings.

The above specimen organic cells may be lymphocytes, for example. The microwell array chip of the present invention can be employed to detect single antigen-specific lymphocytes, for example.

In the microwell array chip of Aspect 1, multiple microwells are arranged horizontally and vertically with equal spacing and markers are desirably provided at a prescribed number of microwells. In particular, the microwell array chip of Aspect 1 is divided into groups each comprised of a prescribed number of microwells. These groups are provided on the principal surface of the substrate, and markers are provided so that the position of each group can be determined.

Figure 1:
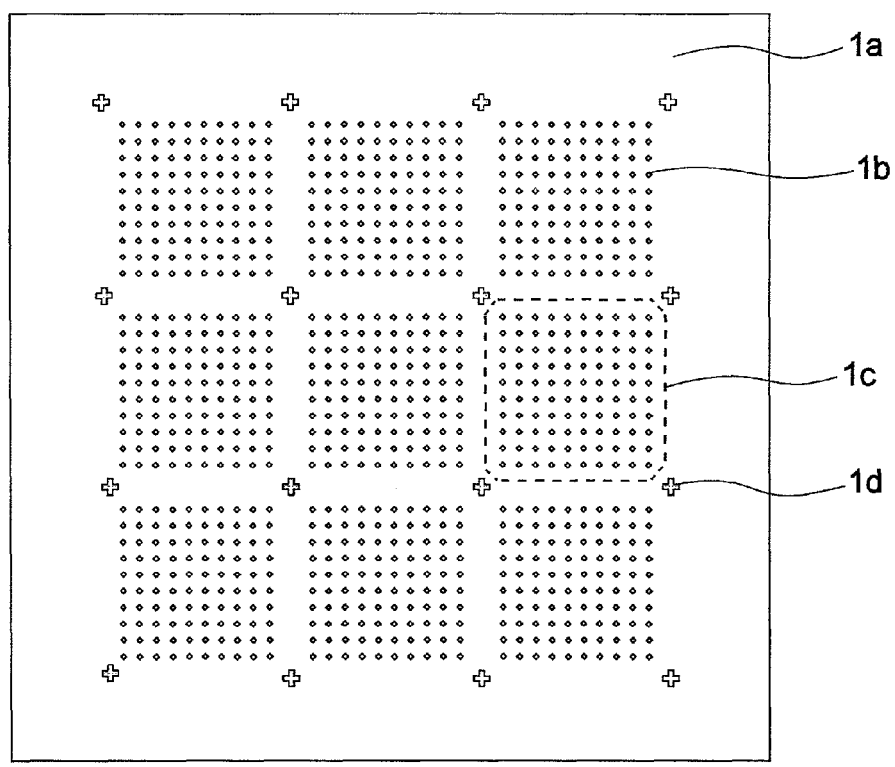
FIG. 1 is a plan view of a microwell array chip 1*a* on which are provided three horizontal and three vertical groups 1*c* of 10×10 microwells 1*b*.

For example, FIG. 1 shows a plan view of a microwell array chip 1*a* on which three horizontal and three vertical groups 1*c* of 10×10 microwells 1*b* are provided. A marker 1*d* is provided on each of the four corners of 10×10 microwell groups 1*c*. It is also possible to provide markers on the four corners of the overall microwell array chip 1*a* to distinguish the markers provided on the four corners of each group.

The number of microwells making up a single group of microwells is not specifically limited, and may range, for example, from 10 to 10,000.

The markers may be used simply to identify position, or may be numbers or letters. The use of markers in the form of numbers or letters not only determines the position of each group, but can also specify each group. That is, a number can be assigned to each group.

The markers may be legible by fluorescence microscope or image scanner, for example. Thus, they are desirably comprised of a fluorescent material or reflective material.

Specific examples of fluorescent materials are materials emitting fluorescence at a prescribed wavelength when excited by light entering from the exterior. A material suited to processing by photolithography, a technique for manufacturing semiconductor integrated circuits lending itself to the use of thin films, is desirably selected. Examples are o-naphthoquinone diazide-novolak type resists, with Tokyo Ohka Kogyo (K.K.) OFPR-800 being preferred.

Further, a processed substrate material and a thin-film formed on a substrate are selected as reflective materials. By processing the substrate material by etching, pressing, or the like, for example, a reflective structure having an incline relative to the surface or an identification pattern having characters or information can be formed. By forming a thin film on the substrate material and fabricating a rise and dip structure by processing such as etching, it is possible to form an irregularly reflecting structure based on minute indentations and protrusions on the surface of the thin film or inclines in the edge surfaces of the thin film, achieving the same effect as described above.

When observing the sample in the microwell with fluorescence, portions not emitting fluorescence are completely invisible. Thus, to determine the position of the sample on the substrate, a fluorescent label is required.

Neither the shape nor the size of the microwells is specifically limited. However, for example, the shape of the microwell can be cylindrical. It can also be noncylindrical, such as a polyhedron comprised of multiple faces (for example, a parallelepiped, hexagonal column, or octagonal column), an inverted cone, an inverted pyramid (inverted triangular pyramid, inverted square pyramid, inverted pentagonal pyramid, inverted hexagonal pyramid, or an inverted polygonal pyramid with seven or more angles), or have a shape combining two or more of these shapes. For example, it may be partly cylindrical, with the remainder having the shape of an inverted cone. In the case of an inverted conical or an inverted pyramidal shape, the mouth of the microwell is on the bottom. However, the shape may be one in which a portion of the top of an inverted cone or inverted pyramid is cut off (in which case the bottom of the microwell is flat). For conical and parallelepiped shapes, the bottom of the microwell is normally flat, but curved surfaces (convex or concave) are also possible. The reason the bottom of the microwell is made curved is the same as for shapes consisting of an inverted cone or inverted pyramid with a portion of the top cut off.

The shape and size of the microwell are suitably determined in consideration of the type of organic cell (shape, size, and the like of the organic cell) to be stored in the microwell so that a single organic cell will be contained per microwell.

To ensure that a single organic cell will be contained per microwell, for example, the diameter of the largest circle that can be inscribed in the planar shape of the microwell suitably falls within a range of 0.5 to 2-fold, desirably 0.8 to 1.9-fold, and preferably, 0.8 to 1.8-fold the diameter of the organic cell to be contained in the microwell.

Further, the depth of the microwell suitably falls within a range of 0.5 to 4-fold, desirably 0.8 to 1.9-fold, and preferably, 0.8 to 1.8-fold the diameter of the organic cell to be contained in the microwell.

For a cylindrically-shaped microwell, the dimensions can be, for example, a diameter of 3 to 100 micrometers. When the organic cell is a B lymphocyte, the diameter is desirably 4 to 15 micrometers. Further, the depth can be from 3 to 100 micrometers, and in the case where the organic cell is a B lymphocyte, the depth is desirably 4 to 40 micrometers. However, the dimensions of the microwell, as set forth above, can be suitably determined in consideration of a desirable ratio of the diameter of the organic cell to be contained in the microwell to the dimensions of the microwell.

The number of microwells present in a single microwell array chip is not specifically limited. However, when the organic cell is a lymphocyte and the frequency of a given antigen-specific lymphocyte per $10^5$ cells is from 1 to about 500 at the high end, the number of microwells can range from about 2,000 to 1,000,000 per $cm^2$, for example.

In Aspect I, the shape of the surface of the inner wall of the microwell is desirably smooth so as to permit smooth removal of cells. The height of dips and rises on the surface can fall within a range of 0 to 1.0 micrometer, preferably a range of 0 to 0.5 micrometer, and more preferably, a range of 0 to 0.1 micrometer.

There can be differences in the height of dips and rises at any position on the inner wall of a microwell. By creating dips and rises on a portion of the inner wall of a well that has been treated for smoothness, functionality can be added to the well. For example, creating a protrusion of 0.5 to 1 micrometer in height in the vicinity of the entrance to the well makes it difficult for a cell within the well to flow out during washing. This mode corresponds to Aspect II described further below. Imparting protrusions to the bottom surface of a well allows a cell to be supported by the protrusions and thus not come into contact with the bottom surface of the well.

The inner wall of a microwell can be smoothed by etching. The degree of vacuum in the etching device, the type of etching gas, the etching steps, and the like can be suitably selected. For example, when smoothing the inner wall of a microwell with a Multiplex ASE etching device made by STS Corporation, the process cycle time of the etching step and the protective film forming step are desirably suitably selected. Smoothing of the inner wall of a microwell can be conducted by wet etching or by combining a hot oxidation step with oxide film etching.

For example, when varying the height of dips and rises at some position on the inner wall of a microwell with a Multiplex ASE etching device made by STS Corporation, the process cycle of the device can be varied to form dips and rises of desired height at desired positions on the inner wall of the microwell. In wet etching and the like, this can be achieved by suitably selecting the type, concentration, and temperature of the chemical solution.

Protrusions can also be formed at specific sites on the well sidewall by etching. For example, by extending the process cycle time at a position at which the formation of a protrusion is desired using a Multiplex ASE etching device made by STS Corporation, a protrusion of desired height can be formed at a desired position on the well sidewall. Protrusions can also be formed by suitably selecting and varying the etching conditions at positions at which the formation of protrusions is desired using etching devices other than the above etching device.

The microwell array chip of Aspect I can be made of silicon, metal, or resin, for example. When made of silicon, silicon processing technology, which is currently the mainstream fabrication technology for semiconductor integrated circuits, can be applied without modification. Thus, the use of silicon is superior to the use of other materials from the perspectives of microprocessing properties, mass production properties, and integration with future analytical circuits such as sensors.

Examples of the above metal are aluminum, stainless steel, copper, nickel, chromium, and titanium.

Examples of the above resin are polyimide, polyethylene, vinyl chloride, polypropylene, polycarbonate, acrylic, and polyethylene terephthalate.

The method for manufacturing a microwell array chip made of silicon with markers of a fluorescent material will be described.

(1) A fluorescent substance (for example, Tokyo Ohka OFPR-800) is coated on a principal surface of a silicon substrate. The fluorescent substance may be suitably selected from among materials other than Tokyo Ohka OFPR-800 so long as the material selected has the characteristic of absorbing excitation radiation and releasing energy in the form of fluorescence in the course of returning from the resulting excited state to a base state. The ability to be processed by photolithography is desirable. For example, AZP1350 made by Clariant Corporation may be employed.

(2) A label pattern is formed by photolithography on the surface and hardening processing is conducted at elevated temperature (for example, 180° C.) to increase the resistance of the fluorescent substance to solvents. The temperature used in the hardening process can be suitably selected based on the fluorescent substance.

(3) After hardening processing, a microwell pattern is formed by photolithography and hardening is conducted at low temperature (not greater than 100° C.). The microwell pattern can be suitably determined based on the microwell dimensions, arrangement, and the like. The hardening temperature can be suitably determined based on the photoresist material employed in the microwell pattern.

(4) Wells are formed by dry etching or the like. A known dry etching method may be suitably used to form the wells.

(5) The photoresist employed as a well pattern mask is removed with an organic solvent such as acetone. The organic solvent employed is not limited to acetone. Any organic solvent capable of removing the photoresist may be suitably employed.

Removing the photoresist leaves behind on the chip just the microwells and the fluorescent labels formed on the silicon substrate, yielding the microwell array chip of Aspect I.

The method for manufacturing a microwell array chip made of silicon with markers of a reflective material will be described next.

(1) Photolithography is used to form a label pattern on a principal surface of a silicon substrate. When manufacturing a reflective structure out of a thin film, it is necessary to form a thin film of material on the same surface prior to photolithography.

(2) An inverted pyramidal reflective structure is made, for example, by etching comprising, for example, immersion in an alkali solution having anisotropic surface etching characteristics. For a thin film, an etching method is suitably selected.

(3) A microwell pattern is formed by photolithography. The microwell pattern is suitably determined based on the dimensions and arrangement of the microwells.

(4) The wells are formed by a dry etching method or the like. A known dry etching method may be suitably used to form the wells.

(5) A photoresist separating solution or the like is used to remove the photoresist.

Removing the photoresist leaves behind on the chip just the microwells and reflective labels formed on the silicon substrate, yielding the microwell array of Aspect I.

In the microwell array chip of Aspect I, quantum effects typified by carrier barrier phenomena of electrons and holes, such as photoluminescent structures employing the effects of confined carriers, may be exploited. The photoluminescent material employed may be suitably selected based on the wavelength required. A photoluminescent structure may be added to the chip, or a photoluminescent structure may be built into the chip itself. For example, quantum-effect particles, impurity doping, porous materials, and thin-film lamination-based quantum well structures may be formed or a film of a photoluminescent material may be formed to provide markers on the microwell array chip of Aspect I.

Figure 14:
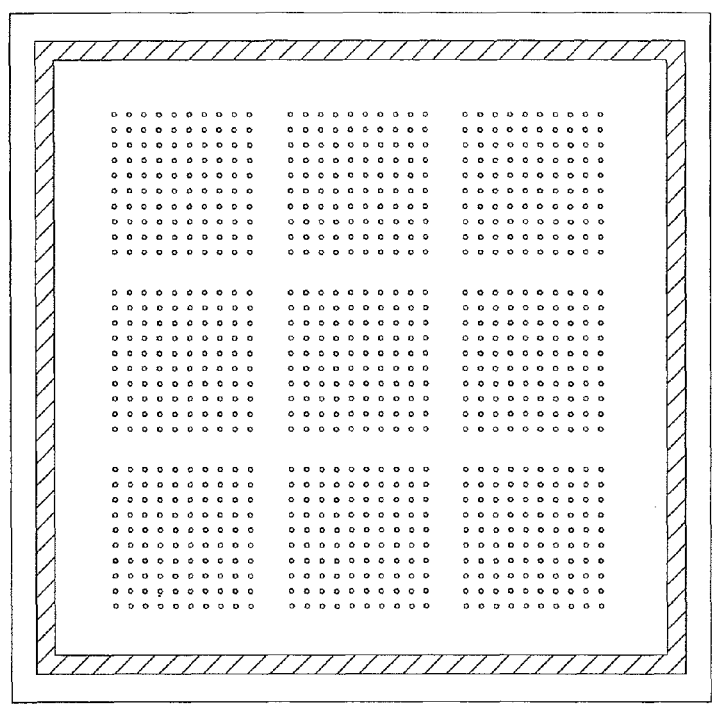
FIG. 14 is a schematic drawing of a microwell array chip having a hydrophobic region provided in a manner surrounding the multiple microwells on a principal surface having multiple microwells.

Further, the microwell array chip of Aspect I may have a hydrophobic region provided in a manner surrounding multiple microwells on a principal surface having multiple microwells. FIG. 14 is a schematic diagram of a microwell array chip on which such a region is provided. As shown in FIG. 14, a hydrophobic region is provided in a manner surrounding the microwells so that the solution containing cells and the like being planted on the microwell array does not cross the hydrophobic region and disperse, thereby permitting efficient concentration of the cell dispersion on the microwells. Such a region may be flat or may be in the form of a groove. The number of such regions is not specifically limited. A single such region may be provided, or two or more may be provided. The width of this region may be suitably established based on the amount of solution being planted; for example, the width may be 100 micrometers to 1 mm. When this region is in the form of a groove, the depth of the groove may be suitably set based on the amount of solution being planted; for example, the depth may be 5 to 100 micrometers.

The hydrophobic region may have a silicon surface or a fluorine-containing surface, for example.

Figure 15:
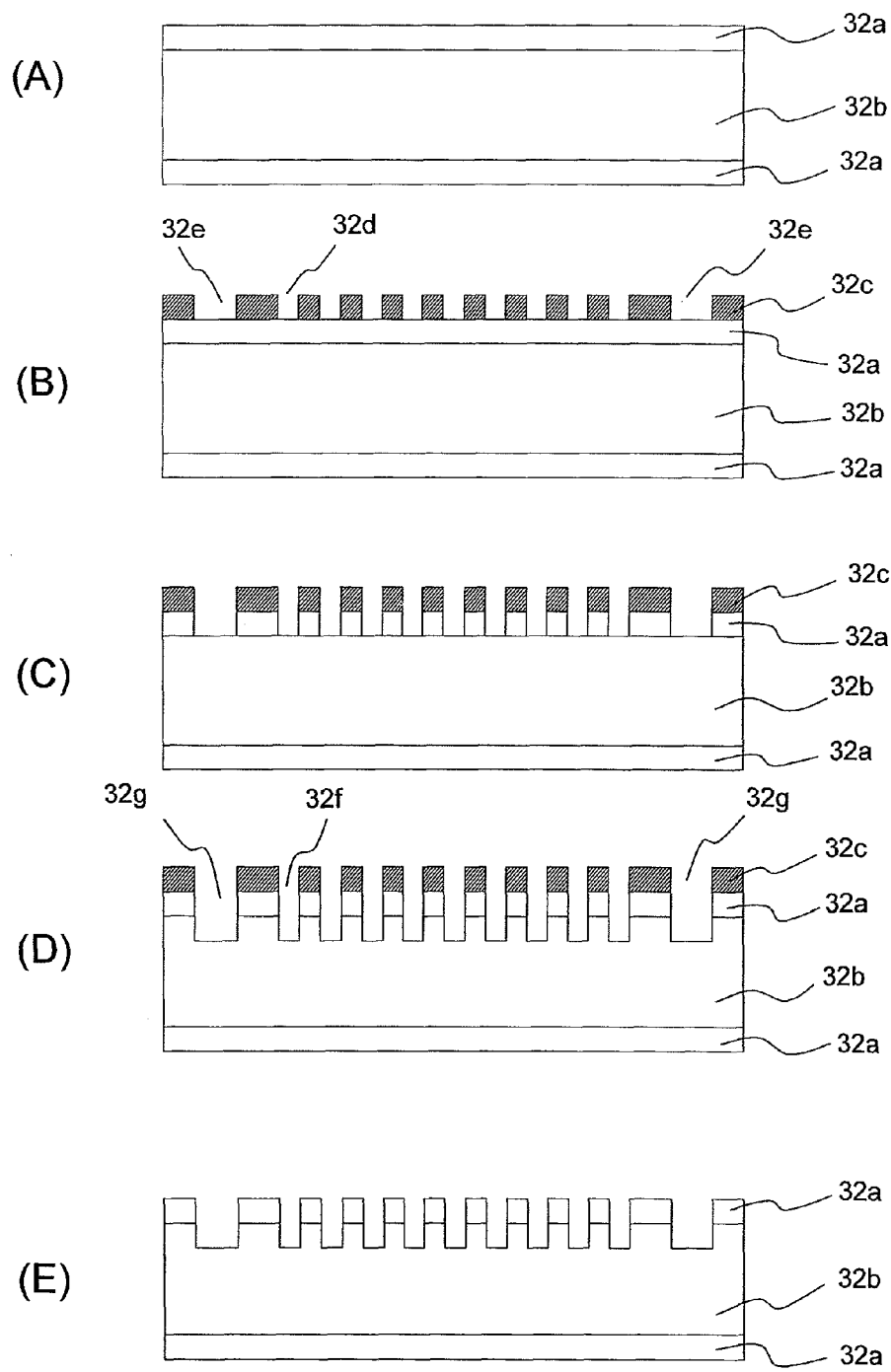
FIG. 15 is a drawing descriptive of the method for manufacturing the microwell array chip shown in FIG. 14.

The method for manufacturing a microwell array chip on which is provided a groove-like hydrophobic region having a silicon surface, the substrate being made of silicon, will be described below by way of example with reference to FIG. 15.

(1) A coating of novolak resin-based positive resist OFPR-800 (32c) made by Tokyo Ohka Kogyo (K.K.), for example, is formed on a silicon substrate 32b (FIG. 15(A)) on which has been formed a silicon oxide film 32a, thus forming a microwell pattern 32d. In this process, the microwell pattern and a pattern 32e providing the groove-like hydrophobic regions are simultaneously formed (FIG. 15(B)).

(2) Exposed silicon oxide film 32a is removed from the pattern by hydrofluoric acid (FIG. 15(C)), and as needed, photoresist 32c is removed. Dry etching employing fluorine-based gas or ion implantation, or wet etching employing an alkali solution or fluonitric acid, is used to etch the silicon. Microwells 32f are formed at this time. At the same time, in the portion in which pattern 32e has been formed, the surface of the hydrophobic silicon is exposed, forming groove-like hydrophobic regions 32g (FIG. 15(D)).

(3) Once the photoresist has been removed, a microwell array chip in which are provided groove-like hydrophobic regions having silicon surfaces surrounding the microwells is obtained (FIG. 15(E)).

Figure 16:
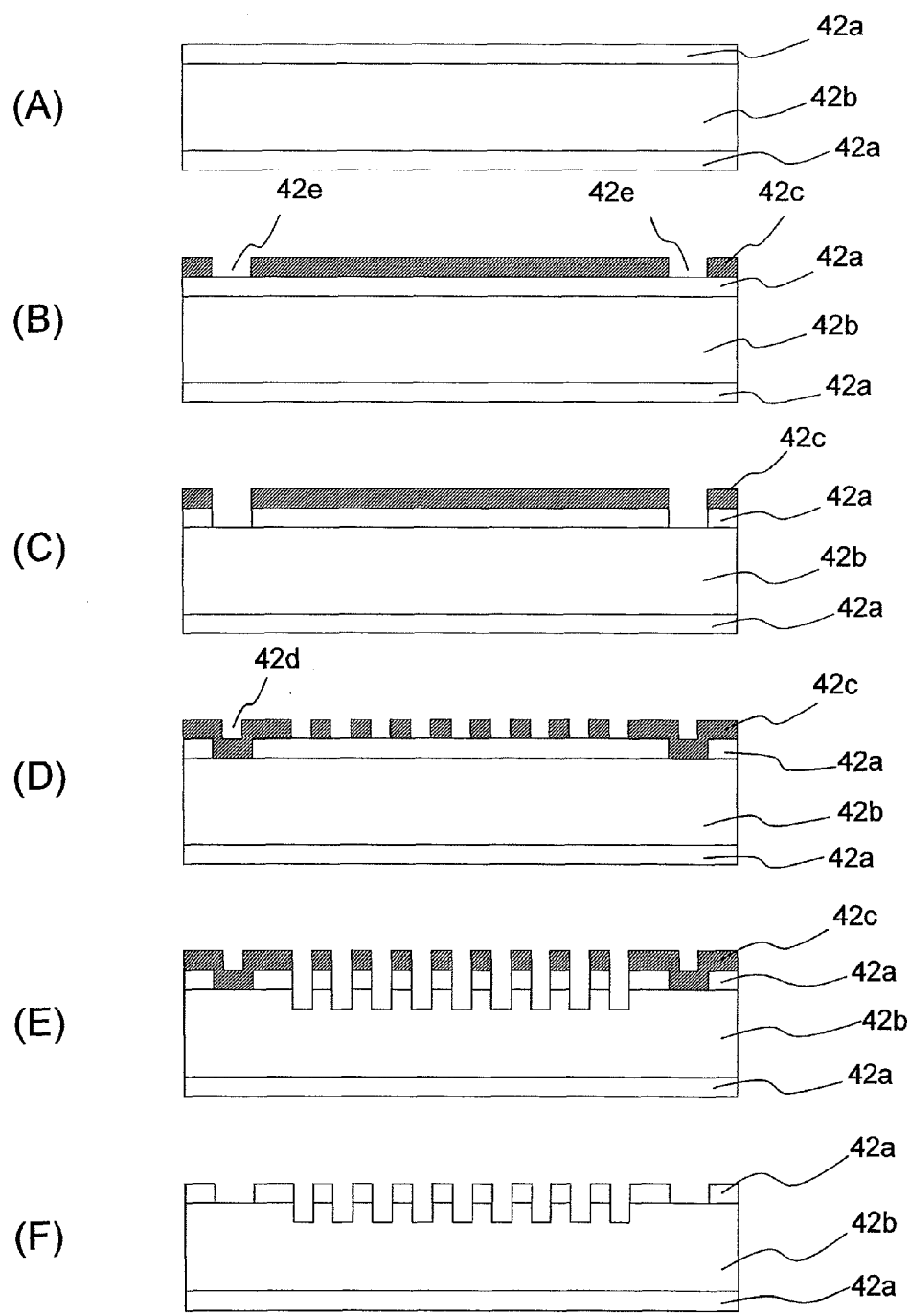
FIG. 16 is a drawing descriptive of the method for manufacturing a microwell array chip provided with a hydrophobic region.

In the present invention, the formation of wells on and etching of the silicon substrate itself as set forth above can yield a microwell array chip on which are provided groove-like hydrophobic regions, as well as a microwell array chip on which are provided groove-like hydrophobic regions in which the silicon surface has been exposed by oxide film etching. An example of a method for manufacturing such a microwell array chip will be described below with reference to FIG. 16.

(1) A coating of novolak resin-based photoresist OFPR-800 (42c) made by Tokyo Ohka Kogyo (K.K.), for example, is applied to a silicon substrate 42b (FIG. 16(A)) on which has been formed a silicon oxide film 42a to form a pattern 42e for providing groove-like hydrophobic regions (FIG. 16(B)).

(2) Exposed silicon oxide film 42a is removed from the pattern with hydrofluoric acid or the like, exposing the silicon (FIG. 16(C)). Here, part of the photoresist is removed.

(3) A coating of photoresist is again applied to the same silicon substrate surface to form microwell pattern 42d (FIG. 16(D)). The exposed silicon oxide film is removed with hydrofluoric acid or the like from the pattern that has been formed.

(4) Dry etching employing fluorine-based gas or ion implantation, or wet etching with an alkali solution or fluonitric acid is used to etch the silicon (FIG. 16(E)).

(5) Removing the photoresist yields a microwell array chip on which are provided groove-like hydrophobic regions having silicon surfaces surrounding the microwells (FIG. 16(F)).

In the hydrophobic regions, fluorine-containing surfaces may be present. Examples of fluorine-containing surfaces are: fluorocarbon surfaces; fluororesin surfaces comprised of carbon, fluorine, hydrogen, and the like; and fluorosilicon surfaces. The hydrophobic regions having fluorine-containing surfaces can be provided by the methods of stamping, printing, or coating a fluorine-based water repellent; the method of forming a groove by etching, for example, and causing a fluorine-based water repellent to flow into the groove; an inkjet method; or a spraycoating method. The hydrophobic regions may also be provided using a silicone resin or paraxylene resins such as parylene. This makes it possible to provide hydrophobic regions even on substrates made of metal or resin.

Method of Marker Use

The excitation radiation employed in a fluorescence detector is irregularly reflected by reflective structures or an irregularly shaped surface. Since a band-pass filter normally eliminating all but the desired fluorescence wavelength is mounted on the detector, the excitation light fully reflected by the chip surface does not enter the detector. However, irregularly reflected light reflects off a mirror having the properties of an initial stage band-pass filter, and can reach the detector. Accordingly, the band-pass filter before the detector in the rear stage is removed during label identification to allow irregularly reflected light to enter the detector. The shape of the label pattern is desirably concave rather than convex to facilitate identification.

Aspect II

Aspect II of the present invention is described below.

The Microwell Array Chip

In the microwell array chip of Aspect II of the present invention, multiple microwells are present on a principal surface of a substrate, the microwells are of a shape and size permitting the storage of only a single organic cell in each microwell, and protruding members are present in the openings of the microwells to narrow the openings.

The protrusions can be formed by causing a film formed on the substrate surface to protrude into the openings. However, the protrusions are not limited to this Aspect. The Aspect of forming the protrusions so that a film provided on the substrate surface protrudes into the openings will be described based on FIG. 7.

FIGS. 7(A) and (B) are a plan view and lateral cross-sectional view, respectively, of an array chip in which a film 12 is provided on the surface of substrate 11 and in which microwells 13 are present. No protrusion is present in opening 13a of microwell 3.

By contrast, FIGS. 7(C), (D), and (E) are a plan view, lateral cross-sectional view, and perspective view, respectively, of an array chip in which a film 12' is provided on the surface of substrate 11 and microwells 13 are present. A protrusion 14 comprised of a portion of film 12' is present in opening 13a of microwell 13.

Figure 7:
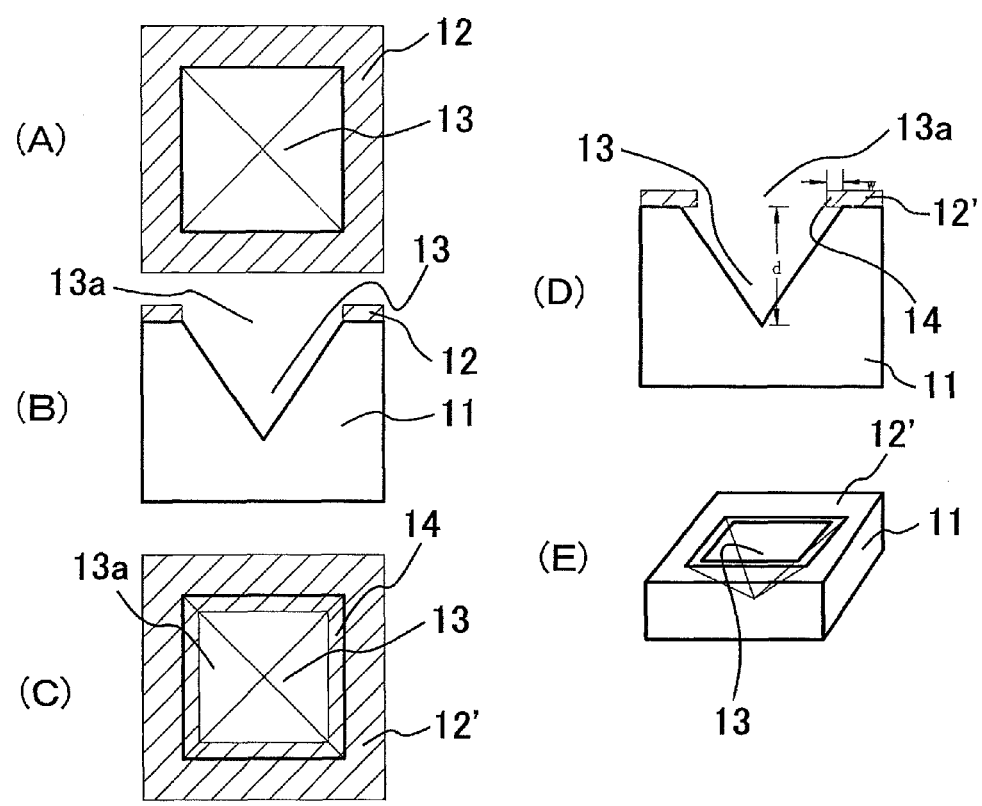
FIGS. 7(A) and (B) are a top view and lateral cross-sectional view, respectively, of an array chip having microwells 13 in which protrusions are not present in openings 13*a*.
FIGS. 7(C), (D), and (E) are a top view, a lateral cross-sectional view, and a perspective view, respectively, of the array chip in which protrusions 14 formed out of portions of film 12' are present in openings 13*a* of microwells 13.

FIGS. 8(A), (B), and (C) are a plan view, lateral cross-sectional view, and perspective view, respectively, of another microwell array chip of Aspect II differing from that of FIG. 7. FIGS. 8(A), (B), and (C) show an array chip in which a film 12" is provided on the surface of substrate 11 and in which microwells 13 are present, with a protrusion 14' formed of part of film 12" being present in the opening 13a of microwell 13. The shape of the opening formed by protrusion 14' is round, in contrast to that of FIG. 7(E) (which is square).

Figure 8:
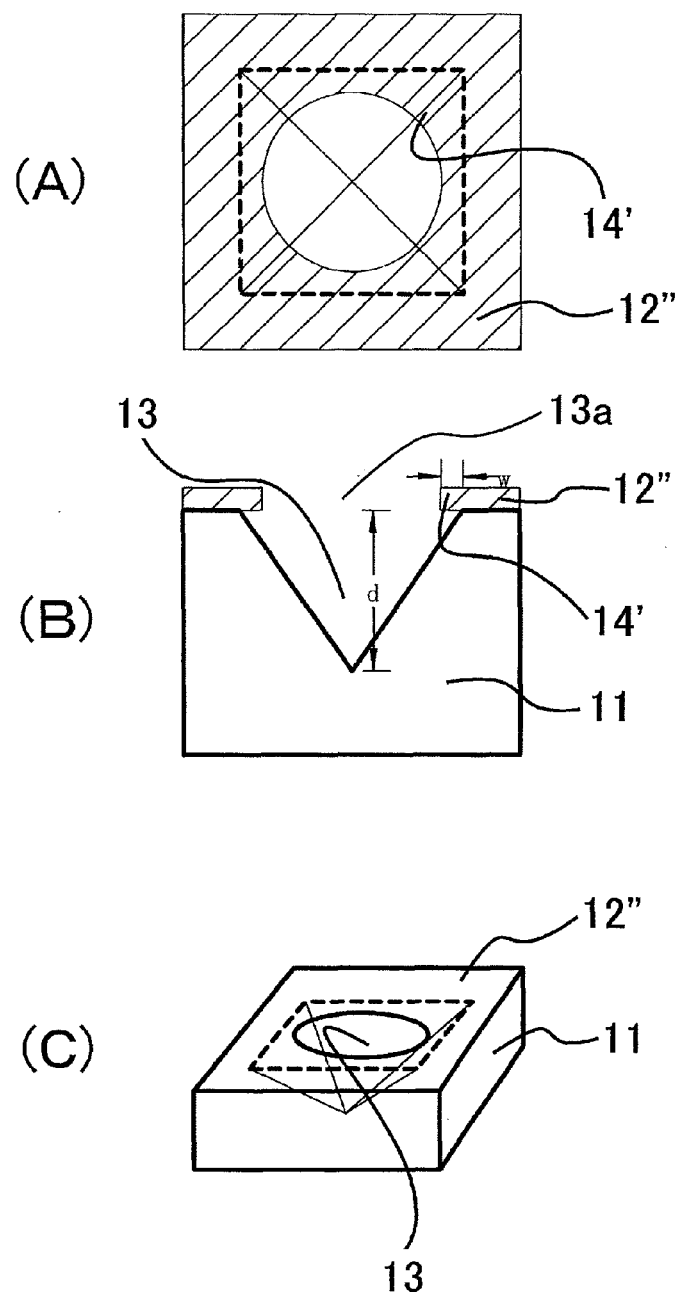
FIGS. 8(A), (B), and (C) are a top view, a lateral cross-sectional view, and a perspective view, respectively, of the microwell array chip of Aspect II of the present invention, which differs from the mode of FIG. 7. Protrusions 14' formed out of portions of film 12" are present in the openings 13*a* of microwell 13, and the openings formed by protrusions 14' are round in shape.

The shape of the opening formed by the protrusion may differ from that of protrusion 14 in FIG. 7 and that of protrusion 14' in FIG. 8. The size of the opening formed by the protrusion is adequate to allow the passage of the organic cell that is to be stored in the microwell.

Figure 9:
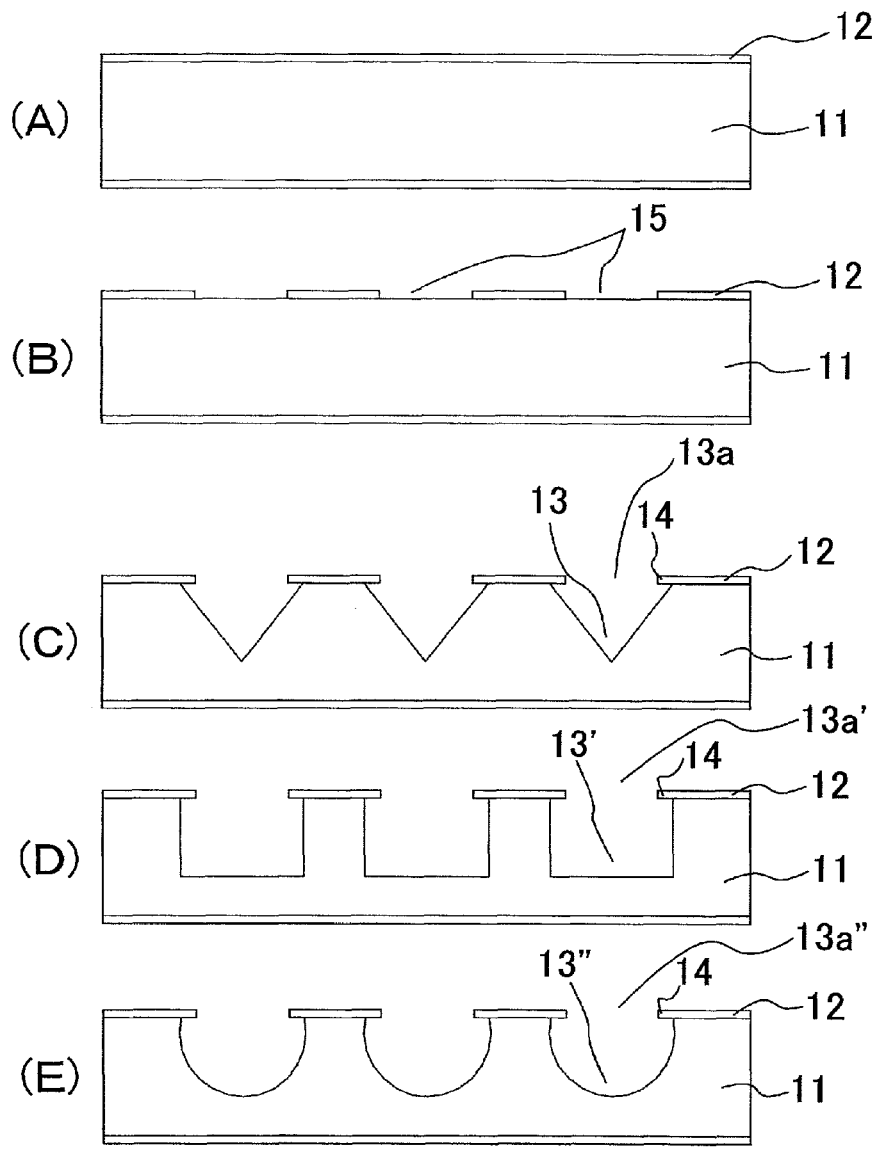
FIGS. 9(A), (B), and (C) are drawings (lateral cross-sectional views) descriptive of the steps of manufacturing a microwell array chip employing a silicon substrate. The microwells of (C) are inverted pyramidal in shape, those of (D) are square, and those of (E) are hemispherical.

FIG. 9 shows lateral cross-sectional views of microwell array chips of Aspect II with differing microwell shapes.

In FIG. 9(C), which is the same Aspect as in FIGS. 7 and 8, the microwell is an inverted pyramid, while the microwell of FIG. 9(D) is square and that of FIG. 9(E) is hemispherical. However, the shape of the microwell is not specifically limited, and shapes other than these are possible.

Neither the shape nor the size of the microwell is specifically limited. However, for example, the shape of the microwell can be cylindrical. It can also be noncylindrical, such as a polyhedron comprised of multiple faces (for example, a parallelepiped, hexagonal column, or octagonal column), an inverted cone, an inverted pyramid (inverted triangular pyramid, inverted square pyramid, inverted pentagonal pyramid, inverted hexagonal pyramid, or an inverted polygonal pyramid with seven or more angles), or have a shape combining two or more of these shapes. For example, it may be partly cylindrical, with the remainder having the shape of an inverted cone. In the case of an inverted conical or an inverted pyramidal shape, the mouth of the microwell is on the bottom. However, the shape may be one in which a portion of the top of an inverted cone or inverted pyramid is cut off (in which case the bottom of the microwell is flat). For conical and parallelepiped shapes, the bottom of the microwell is normally flat, but curved surfaces (convex or concave) are also possible. The reason the bottom of the microwell is made curved is the same as for shapes consisting of an inverted cone or inverted pyramid with a portion of the top cut off.

The shape and size of the microwell are suitably determined in consideration of the type of organic cell (shape, size, and the like of the organic cell) to be stored in the microwell so that a single organic cell will be contained per microwell.

To ensure that a single organic cell will be contained per microwell, for example, the diameter of the largest circle that can be inscribed in the planar shape of the opening formed by the protrusion provided in the opening of the microwell suitably falls within a range of 0.5 to 2-fold, desirably 0.8 to 1.9-fold, and preferably, 0.8 to 1.8-fold the diameter of the organic cell to be contained in the microwell.

Further, the depth of the microwell suitably falls within a range of 0.5 to 4-fold, desirably 0.8 to 1.9-fold, and preferably, 0.8 to 1.8-fold the diameter of the organic cell to be contained in the microwell.

For a cylindrically-shaped microwell, the dimensions can be, for example, a diameter of 3 to 100 micrometers. When the organic cell is a B lymphocyte, the diameter is desirably 4 to 15 micrometers. Further, the depth can be from 3 to 100 micrometers, and in the case where the organic cell is a B lymphocyte, the depth is desirably 4 to 40 micrometers. However, the dimensions of the microwell, as set forth above, can be suitably determined in consideration of a desirable ratio of the diameter of the organic cell to be contained in the microwell to the dimensions of the microwell.

The number of microwells present in a single microwell array chip is not specifically limited. However, when the organic cell is a lymphocyte and the frequency of a given antigen-specific lymphocyte per $10^5$ cells is from 1 to about 500 at the high end, the number of microwells can range from about 2,000 to 1,000,000 per $cm^2$, for example.

In Aspect II, as in Aspect I above, the shape of the surface of the inner wall of the microwell is desirably smooth so as to permit smooth removal of cells. The specific details are identical to those given above for Aspect I.

The substrate of the microwell array chip of Aspect II can be made of silicon, metal, or resin, for example. When made of silicon, silicon processing technology, which is currently the mainstream fabrication technology for semiconductor integrated circuits, can be applied without modification. Thus, the use of silicon is superior to the use of other materials from the perspectives of microprocessing properties, mass production properties, and integration with future analytical circuits such as sensors.

Examples of the metal constituting the substrate are aluminum, stainless steel, copper, nickel, chromium, and titanium.

Examples of the resin constituting the substrate are polyimide, polyethylene, vinyl chloride, polypropylene, polycarbonate, acrylic, and polyethylene terephthalate.

Examples of the film provided on the surface of the substrate are oxide films, nitride films, impurity diffusion layers, metal films, and resin films.

Examples of oxide films are silicon oxide films, silicon oxide nitride films, aluminum oxide films, and titanium oxide films.

Examples of nitride films are silicon nitride films, aluminum nitride films, and titanium nitride films.

An example of an impurity diffusion layer is the distribution of a high concentration of boron into a silicon substrate surface.

Examples of metal films are aluminum, gold, platinum, stainless steel, copper, nickel, chromium, titanium, germanium, and silicon germanium.

Examples of the resin films are polyimide, polyethylene, vinyl chloride, polypropylene, polycarbonate, acrylic, and polyethylene terephthalate.

The thickness of the film provided on the substrate surface is not specifically limited, and may range from 100 nm to 5 micrometers, for example. It desirably falls within a range of from 300 nm to 1 micrometer.

When the substrate is made of silicon, the type of film provided on the substrate surface is desirably an oxide film, nitride film, or impurity diffusion layer from the perspective of being able to apply current mainstream integrated circuit fabrication technology as is and in terms of mass production properties, cost reduction, and reliability.

When the substrate is made of silicon, the film provided on the substrate surface is desirably a resin film from the perspectives of the application of photolithography, etching selection, and mass production properties.

When the substrate is made of silicon, the film provided on the substrate surface is desirably made of metal from the perspectives of the application of photolithography, combination with sensors, film durability, and mass production properties.

When the substrate is made of metal, the film provided on the substrate surface is desirably made of metal from the perspectives of etching selection and enhancing the heat resistance and durability of the film.

When the substrate is made of metal, the film provided on the substrate surface is desirably made of resin from the perspectives of the application of photolithography, etching selection, and the like.

When the substrate is made of metal, the film provided on the substrate surface is desirably an oxide film, nitride film, or the like from the perspectives of ease of film formation and durability and adhesion of the film.

When the substrate is made of resin, the film provided on the substrate surface is desirably made of resin from the perspectives of cost reduction and the ability to use various known forming and processing techniques in manufacturing.

When the substrate is made of resin, the film provided on the substrate surface is desirably made of metal from the perspectives of the functionality, processability, and durability of the film.

The Method for Manufacturing a Microwell Array Chip

The microwell array chip of Aspect II can be manufactured by the following methods, for example:

The method for manufacturing a microwell array chip of Aspect II of the present invention comprising the steps of:

forming a film on at least one principal surface of a substrate;

applying a resist coating on the film that has been formed;

exposing the resist surface through a mask having a microwell pattern and removing uncured portions of resist;

etching the exposed portions of said film and substrate to fabricate wells in the form of a microwell array; and removing the resist.

The case where the substrate is made of silicon will be described below.

(1) A thin film of oxide or the like is formed by a method such as hot CVD or CVD on the surface of a silicon substrate that has been washed.

(2) Resist is coated on the thin film that has been formed.

(3) The resist surface is exposed through a mask having a microwell pattern and the uncured portion of the resist is removed. That is, a microwell pattern is formed on a thin film by photolithography, and the silicon surface is exposed.

(4) The exposed portions of the film and substrate are etched to form wells in the form of a microwell array. The etching can be performed with, for example, an alkali etching solution (for example, TMAH: tetramethyl ammonium hydroxide). In this process, etching advances in the direction of depth of the substrate and beneath the thin film. When etching is conducted for longer than the prescribed time, a lip-shaped protrusion of thin film is formed in the opening of the microwell formed in the silicon substrate.

(5) The resist is removed to obtain the microwell array chip of Aspect II.

The case where the substrate is made of metal will be described next.

(1) A thin film of resin, or a thin film of metal having etching selectivity with the substrate, is formed on the surface of a washed metal substrate, or the surface of the metal substrate is subjected to an oxidation or nitridation treatment to form a thin film.

(2) Photoresist is coated on the thin film that has been formed.

(3) The surface of the photoresist is exposed through a photomask having a microwell pattern and the uncured portion of the photoresist is removed. That is, photolithography is used to form a microwell pattern in the thin film, exposing the substrate surface.

(4) A method such as etching the exposed portions of the substrate is used to form wells in the form of a microwell array. The etching means employed is suitably selected.

(5) When etching toward the bottom is continued, the area to the sides directly beneath the thin film is also etched somewhat, forming a lip structure.

(6) When the photoresist is removed, the microwell array chip of Aspect II is obtained.

The case where the substrate is made of resin will be described next.

(1) A thin film of resin or metal is formed on a washed resin substrate, or the resin surface is modified to enhance durability or the like. The modification may be accomplished by UV processing, introduction of a modifying material, or the like.

(2) Photoresist is coated on the thin film that has been formed.

(3) The photoresist surface is exposed through a photomask having a microwell pattern and uncured portions of the photoresist are removed. That is, a microwell pattern is formed on the thin film by photolithography and the substrate surface is exposed.

(4) Wells are formed in microwell array form by a method such as dissolving portions of the exposed substrate. At this time, the solution used for etching is suitably selected. Alternatively, if the substrate itself can be subjected to photolithography, for example, it can be exposed to UV radiation using a mask in the form of a metal thin film in a microwell pattern and the exposed portions removed. At this time, the depth of the wells can be controlled by the level of UV exposure.

(5) Here, when dissolving toward the bottom is continued, the area to the sides directly beneath the thin film is also etched somewhat, forming a lip structure.

(6) When the photoresist is removed, the microwell array chip of Aspect II is obtained.

The case where an oxide film is provided on the surface of a silicon substrate will be described next.

(1) An oxide film (silicon oxide film or the like) is formed by a method such as hot oxidation, hot CVD, or plasma CVD on a washed silicon substrate.

(2) Photoresist is coated on the thin film that has been formed.

(3) The photoresist surface is exposed to UV through a mask having a microwell pattern and the uncured portions of the photoresist are removed. That is, photolithography is used to form a microwell pattern on the thin film, exposing the silicon surface. The photoresist is removed.

(4) Wells are formed in microwell array form by etching the exposed portion of the substrate. For example, etching can be conducted with an alkali etching solution (for example, TMAH: tetramethyl ammonium hydroxide). When etching is continued in the direction of thickness of the substrate, etching also continues in the area to the sides directly beneath the thin film. When etching is conducted for a period exceeding the conventional period, eave-shaped protrusions of thin film are formed in the entrances to the microwells that have been formed on the silicon plate.

(5) A microwell array chip of Aspect II is thus obtained.

The case where a metal thin film is provided on the surface of a silicon substrate will be described next.

(1) A metal thin film is formed on a silicon substrate by CVD, resistive hot vapor deposition, sputtering vapor deposition, e-beam vapor deposition, or the like.

(2) Photoresist is coated on the thin film that has been formed.

(3) The photoresist surface is exposed to UV through a mask having a microwell pattern and the uncured portions of photoresist are removed. That is, photolithography is used to form a microwell pattern on the thin film, exposing the silicon surface. At this time, the method of etching the thin film to form the pattern is suitably selected. For example, for aluminum, a mixed acid of phosphoric acid, nitric acid, acetic acid, and water may be employed. When necessary, the photoresist may be removed.

(4) Wells are formed in microwell array form by etching the exposed portions of the substrate. Etching can be conducted with an alkali etching solution, for example. The etching solution is suitably selected. For example, when fabricating a structure based on an aluminum thin film, an etching solution that etches silicon but not aluminum (for example, hydrazine hydrate is selected; hydrazine does not corrode most metals) is employed. When the etching is conducted in the direction of thickness of the substrate, it also proceeds to the sides directly beneath the thin film. When etching is conducted beyond the prescribed period, eave-shaped protrusions of thin film are formed in the entrances to the microwells formed on the silicon substrate.

(5) A microwell array chip of Aspect II is thus obtained.

The case where a resin thin film is provided on the surface of a silicon substrate will be described next.

(1) A resin thin film is formed by CVD, coating, dipping, or a similar method on a washed silicon substrate.

(2) Photoresist is coated on the thin film that has been formed. The photoresist surface is exposed to UV radiation through a mask having a microwell pattern and the uncured portions of the photoresist are removed. That is, photolithography is employed to form a microwell pattern on the thin film, exposing the silicon surface. At this time, the method used to remove the resin thin film to form the pattern is suitably selected. For example, when employing a photosensitive polyimide thin film, the pattern can be formed directly in the resin thin film that has been coated, so the photoresist application step can be omitted and the resin thin film processed by exposure alone.

(3) The exposed portions of the substrate are etched to form wells of microwell array form. The etching can be conducted, for example, with an alkali etching solution. The etching solution is suitably selected. For example, for a polyimide thin film, hydrazine hydrate or ethylene diamine pyrocatechol can be selected. At this time, when etching is conducted in the direction of thickness of the substrate, etching continues to the sides directly beneath the thin film. When etching is conducted beyond the prescribed period, eave-shaped protrusions of thin film are formed in the entrances to the microwells formed in the silicon substrate.

(4) This yields a microwell array chip of Aspect II.

The case where a silicon nitride film is provided on the surface of a silicon substrate will be described next.

(1) A silicon nitride thin film is formed by CVD, sputtering vapor deposition, or the like on a washed silicon substrate.

(2) Photoresist is coated on the thin film that has been formed.

(3) The photoresist surface is exposed to UV through a mask having a microwell pattern and the uncured portions of photoresist are removed. That is, photolithography is used to form a microwell pattern on the thin film, exposing the silicon surface. The photoresist is removed.

(4) Wells are formed in microwell array form by etching the exposed portions of the substrate. For example, an alkali etching solution (for example, TMAH: tetramethyl ammonium hydroxide is employed in etching). At this time, when etching is conducted in the direction of thickness of the substrate, etching continues to the sides directly beneath the thin film. Here, when etching is conducted beyond the prescribed period, eave-shaped protrusions of thin film are formed in the entrances to the microwells formed on the silicon substrate.

(5) This yields a microwell array chip of Aspect II.

The case in which an impurity diffusion layer is provided on a silicon substrate will be described next.

(1) Photoresist is coated on a washed silicon substrate. The photoresist surface is exposed to UV through a mask having a microwell pattern and the uncured portions of the photoresist are removed. That is, photolithography is used to form a microwell pattern on the thin film, exposing the silicon surface everywhere but in well pattern portions.

(2) The substrate is washed and a high concentration of boron (about $10^{20}/cm^2$) is diffused into the exposed portions of silicon by hot diffusion, ion implantation, or the like. A diffusion source other than boron, such as germanium or silicon germanium, may also be employed. The thickness of the diffusion layer can be controlled by a heat treatment (drive-in) to achieve deep diffusion. In this process, oxygen is introduced into a heat treatment furnace to form a silicon oxide film on the surface.

(3) Well etching can be conducted with, for example, an alkali etching solution (such as TMAH: tetramethyl ammonium hydroxide). At this time, the silicon surface into which boron has not diffused etches readily, while the silicon surface where boron has been diffused to high concentration tends not to etch. Thus, etching can proceed selectively in well pattern portions where boron has diffused. When etching is performed in the direction of thickness of the substrate, the etching proceeds to the sides directly beneath the thin film. When etching is conducted beyond the prescribed time, lip-shaped protrusions are formed in the entrances to the microwells formed on the silicon substrate.

(4) This yields a microwell array chip of Aspect II.

The microwell array chip of Aspect II may also have hydrophobic regions provided in such a manner as to surround the multiple microwells on the principal surface having multiple microwells. The specific details of these regions are as described for Aspect I above.

Aspect III

Aspect III of the present invention is described below.
The Microwell Array Chip The microwell array chip of Aspect III of the present invention is a microwell array chip made of silicon and having multiple microwells, each microwell being used to store a single specimen organic cell, wherein each microwell is of a size and shape capable of holding just one organic cell.

The above specimen organic cell can be a lymphocyte, for example. The microwell array chip of the present invention can be used to detect individual antigen-specific lymphocytes.

Neither the size nor the shape of the microwells is specifically limited. However, for example, the shape of the microwell can be cylindrical. It can also be noncylindrical, such as a polyhedron comprised of multiple faces (for example, a parallelepiped, hexagonal column, or octagonal column), an inverted cone, an inverted pyramid (inverted triangular pyramid, inverted square pyramid, inverted pentagonal pyramid, inverted hexagonal pyramid, or an inverted polygonal pyramid with seven or more angles), or have a shape combining two or more of these shapes. For example, it may be partly cylindrical, with the remainder having the shape of an inverted cone. In the case of an inverted conical or an inverted pyramidal shape, the mouth of the microwell is on the bottom. However, the shape may be one in which a portion of the top of an inverted cone or inverted pyramid is cut off (in which case the bottom of the microwell is flat). For conical and parallelepiped shapes, the bottom of the microwell is normally flat, but curved surfaces (convex or concave) are also possible. The reason the bottom of the microwell is made curved is the same as for shapes consisting of an inverted cone or inverted pyramid with a portion of the top cut off.

The shape and size of the microwell are suitably determined in consideration of the type of organic cell (shape, size, and the like of the organic cell) to be stored in the microwell so that a single organic cell will be contained per microwell.

To ensure that a single organic cell will be contained per microwell, for example, the diameter of the largest circle that can be inscribed in the planar shape of the microwell suitably falls within a range of 0.5 to 2-fold, desirably 0.8 to 1.9-fold, and preferably, 0.8 to 1.8-fold the diameter of the organic cell to be contained in the microwell.

Further, the depth of the microwell suitably falls within a range of 0.5 to 4-fold, desirably 0.8 to 1.9-fold, and preferably, 0.8 to 1.8-fold the diameter of the organic cell to be contained in the microwell.

For a cylindrically-shaped microwell, the dimensions can be, for example, a diameter of 3 to 100 micrometers. When the organic cell is a B lymphocyte, the diameter is desirably 4 to 15 micrometers. Further, the depth can be from 3 to 100 micrometers, and in the case where the organic cell is a B lymphocyte, the depth is desirably 4 to 40 micrometers. However, the dimensions of the microwell, as set forth above, can be suitably determined in consideration of a desirable ratio of the diameter of the organic cell to be contained in the microwell to the dimensions of the microwell.

The number of microwells present in a single microwell array chip is not specifically limited. However, when the organic cell is a lymphocyte and the frequency of a given antigen-specific lymphocyte per $10^5$ cells is from 1 to about 500 at the high end, the number of microwells can range from about 2,000 to 1,000,000 per $cm^2$, for example.

As in Aspects I and II, the shape of the surface of the inner wall of the microwell in Aspect III is desirably smooth so as to permit smooth removal of cells. The specific details are as described for Aspect I.

The microwell array chip of Aspect III of the present invention is made of silicon. The use of silicon permits the application as is of the silicon processing techniques that are the mainstream of current semiconductor integrated circuit manufacturing techniques. In particular, silicon is better than other materials in terms of its micromanufacturing properties, mass production properties, and future integration with analysis circuits, including sensors.

Since the microwell array chip of Aspect III is made of silicon, the fact that a film of silicon oxide covers the substrate surface is desirable from the perspectives of the hydrophilic property of the chip surface, the stability of the film, and mass production properties. A silicon surface is normally hydrophobic, having the property of repelling cell suspension solution during planting of the cell suspension solution and some-times impeding the storage of organic cells in the microwells. Accordingly, a silicon oxide film is desirable from the perspectives of having a greater hydrophilic property than silicon and affording film stability.

In the microwell array chip of Aspect III, the inner surface of the microwells is desirably covered with a fluorocarbon film or silicon oxide film. Forming an inert, exclusive surface such as a fluorocarbon film or silicon oxide film on the inner surface of the microwells is desirable in that it prevents adhesion of the organic cell and facilitates recovery of the organic cell from the microwell.

That is, when handling organic cells in microwells, adhesion of the organic cells to the interior of the microwells is a problem. In particular, the adhesion of organic cells when attempting to recover organic cells within microwells from the microwells is a considerable problem. To solve this problem, in the present invention, a film such as a fluorocarbon film or silicon oxide film is desirably formed in wells that contact organic cells.

Fluorocarbon films are water-repellent films. A water-repellent film is desirably formed only within the wells; the formation of a silicon oxide film (silicon oxide film) such as that set forth above is desirable on surfaces other than the wells of the microwell array chip. Further, although silicon oxide films do not exhibit a water-repellent property such as that of fluorocarbon films, they have an effect in preventing the adhesion of organic cells. In particular, silicon oxide films formed by high-temperature oxidation with dry oxygen are dense. Although they do not have water repellency to the degree of beading water like fluorocarbon films, they have a property that is between a hydrophilic and a hydrophobic property. Since organic cells are normally handled by dispersion in solution, when the microwell array chip as a whole has a water-repellent or hydrophobic surface, it tends to be difficult to store organic cells in the wells. Thus, in the present invention, surfaces other than well surfaces are desirably coated with silicon oxide films, and fluorocarbon films or silicon oxide films are desirably selectively formed just in the wells.

When forming a fluorocarbon film by the usual surface processing methods, the film is formed after the well has been fabricated. Thus, the entire substrate ends up being covered by the fluorocarbon film, becoming a water-repellent surface. Accordingly, the following method is employed in the present invention. This method will be described for the example of a microwell array chip employing a silicon substrate.

A microwell pattern is formed by photolithography on a silicon substrate. The photoresist hardening temperature is not greater than 100° C. Next, a dry etching vacuum device is employed to form the microwells. Once the fabrication of the microwells has been confirmed, a CF-based gas is introduced into the vacuum device and plasma CVD is conducted. The plasma CVD can be conducted using the etching device as is, or in the CVD device of a separate body of equipment. After forming the film for several minutes, the substrate is removed from the vacuum device and immersed in an organic solvent such as methanol or acetone. This lifts off both the microwell pattern mask and the fluorocarbon film on it, leaving a fluorocarbon film only on the inner wall of the microwell. The etching and film forming steps can be conducted in the same device by simply changing the type of gas employed.

Instead of a fluorocarbon film, the inner surface of the wells can be coated with a silicon oxide film, as set forth above. An improved effect on the recovery rate of organic cells from the wells can be achieved even when the inner surface of the wells is covered with a silicon oxide film instead of a fluorocarbon film.

The method of covering the inner surface of the wells with a silicon oxide film will be described below.

In this case, a well pattern is formed, the photoresist is removed, and a hot oxide film or the like is formed to obtain a microwell array chip in which the inner surface of the wells is coated with a silicon oxide film.

It is also possible to obtain a microwell array chip in which adhesion of organic cells to the inner surface of the wells is prevented by forming porous silicon inside the wells instead of a fluorocarbon film or silicon oxide film. Porous silicon can be produced by a method such as anodizing the inner surface of the wells.

In addition to fluorocarbon films, silicon oxide films, and porous silicon, the microwell array chip of the present invention can be treated, or a film can be formed, to inhibit active silicon surfaces.

In the microwell array chip of Aspect III, hydrophobic regions can be provided in a manner surrounding multiple microwells on a surface having multiple microwells. The specific details of these hydrophobic regions are as set forth above in Aspect I. Further, in the microwell array chip of Aspect III as set forth above, such regions may also be coated with a fluorocarbon film to form hydrophobic regions in the course of coating the inner surface of the microwells with a fluorocarbon film.

EMBODIMENTS

Embodiment 1

Fluorescent Marker

FIG. 1 is an example of a Aspect of implementing the device of Aspect I of the present invention.

FIG. 1 shows a microwell array chip in which multiple microwells $1b$ have been formed on a substrate surface $1a$ of silicon material. Microwells $1b$ form clusters $1c$ of suitable numbers of units (for example, 10×10=100) to facilitate position identification. One use of the present microwell array chip is the introduction of a cell to which a fluorescent substance has been added into each well for evaluation, and the determination of fluorescent emission. In this process, those cells not emitting fluorescence cannot be observed because observation by fluorescence microscope or fluorescence scanner is conducted with specifications based on the wavelength of fluorescence. Accordingly, as shown in FIG. 1, a minute marker $1d$ of a fluorescent substance is formed between the individual clusters.

The method of manufacturing these markers is given below (FIG. 2(A), FIG. 2(B), FIG. 2(C), FIG. 2(D), FIG. 2(E), FIG. 2(F), FIG. 2(G), FIG. 2(H), FIG. 2(I), FIG. 2(J), FIG. 2(K) and FIG. 2(L)).

Two methods of manufacturing microwells in which markers are formed on a substrate of a silicon material or the like will be described.

Marker Manufacturing Method (I)

Figure 2A:
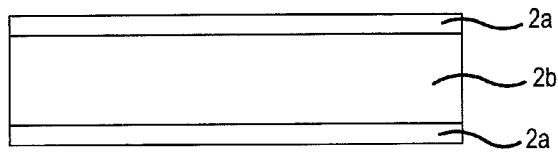
FIG. 2(A), (B), (C), (D), (E), (F), (G), (H), (I), (J), (K) and (L) are drawings descriptive of the method for manufacturing a microwell array chip of Aspect I of the present invention having a fluorescent marker in Embodiment 1.
Figure 2B:
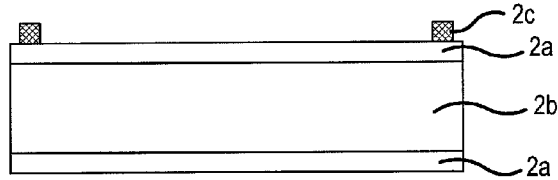

(1) Novolak resin-based positive photoresist OFPR-800 made by Tokyo Ohka Kogyo (K.K.), for example, is coated on a silicon substrate $2b$ (FIG. 2(A)) having a silicon oxide film $2a$, and a marker pattern $2c$ is formed on the substrate (FIG. 2(B)).

(2) The substrate is hardened for 30 minutes at 180° C. and otherwise processed to enhance the chemical resistance of the photoresist by hot crosslinking and the like.

Figure 2C:
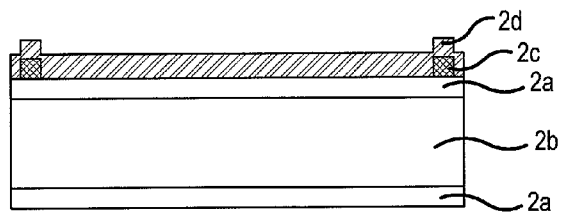
Figure 2D:
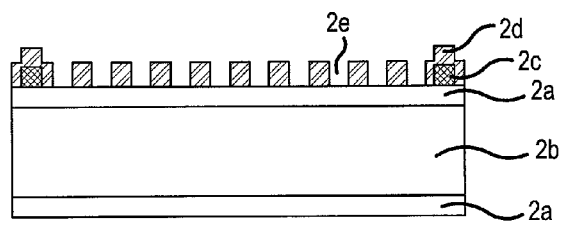

(3) Photoresist $2d$ is again applied to form an opening pattern $2e$ required for manufacturing microwells on silicon substrate $2b$ (FIGS. 2(C) and FIG. 2(D)). At this time, hardening following development is conducted at a low temperature of from about 100 to 110° C.

(4) Hydrofluoric acid is used to remove the silicon oxide film 2a in opening portions, exposing the silicon.

Figure 2E:
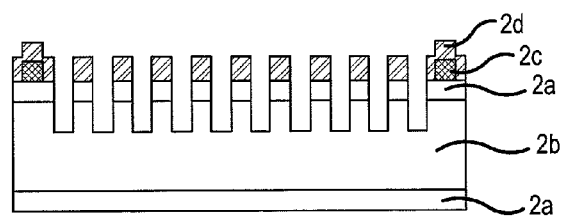

(5) Dry etching is then employed to etch silicon substrate 2b, producing microwells 2f (FIG. 2(E)).

Figure 2F:
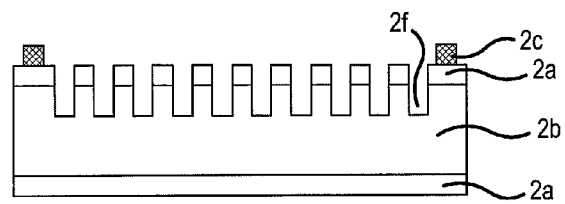

(6) The photoresist 2d applied in (3) is removed with methanol, acetone, or the like, yielding a microwell array chip of Aspect I (FIG. 2(F)).

Marker Manufacturing Method (II)

(1) Novolak resin-based positive photoresist OFPR-800 made by Tokyo Ohka Kogyo (K.K.), for example, is coated on a silicon substrate 2b (FIG. 2(G)) having a silicon oxide film 2a, and a marker pattern 2c is formed on the substrate (FIG. 2(H)).

(2) The substrate is annealed for 30 minutes at 180° C. and otherwise processed to enhance the chemical resistance of the photoresist by hot crosslinking and the like.

(3) Photoresist 2d is again applied to form an opening pattern 2e required for manufacturing microwells on silicon substrate 2b (FIGS. 2(I) and FIG. 2(J)). At this time, heat treatment following development is conducted at a low temperature of from about 100 to 110° C.

(4) Hydrofluoric acid is used to remove the silicon oxide film 2a in opening portions, exposing the silicon (FIG. 2(K)).

(5) The photoresist forming the well pattern is then removed with an organic solvent such as acetone.

(6) Using silicon oxide film 2a on silicon substrate 2b as a mask, a method such as dry etching is used to etch silicon substrate 2b and form microwells 2f, thereby yielding a microwell array chip of Aspect I (FIG. 2(L)).

Based on marker manufacturing method (II), in the course of removing the photoresist after well formation, the photoresist does not denature and become difficult to remove in the dry etching step. Further, the silicon substrate surface that is formed yields an ultrahydrophilic surface due to a plasma effect.

The above steps readily produce a shape such as that shown in FIG. 2(A), FIG. 2(B), FIG. 2(C), FIG. 2(D), FIG. 2(E), FIG. 2(F), FIG. 2(G), FIG. 2(H), FIG. 2(I), FIG. 2(J), FIG. 2(K) and FIG. 2(L). The pattern of marker 2c may be freely selected from among designs, codes, characters, and the like. It is also possible to display information other than markers on the microchip.

Embodiment 2

Reflective Marker

Figure 3:
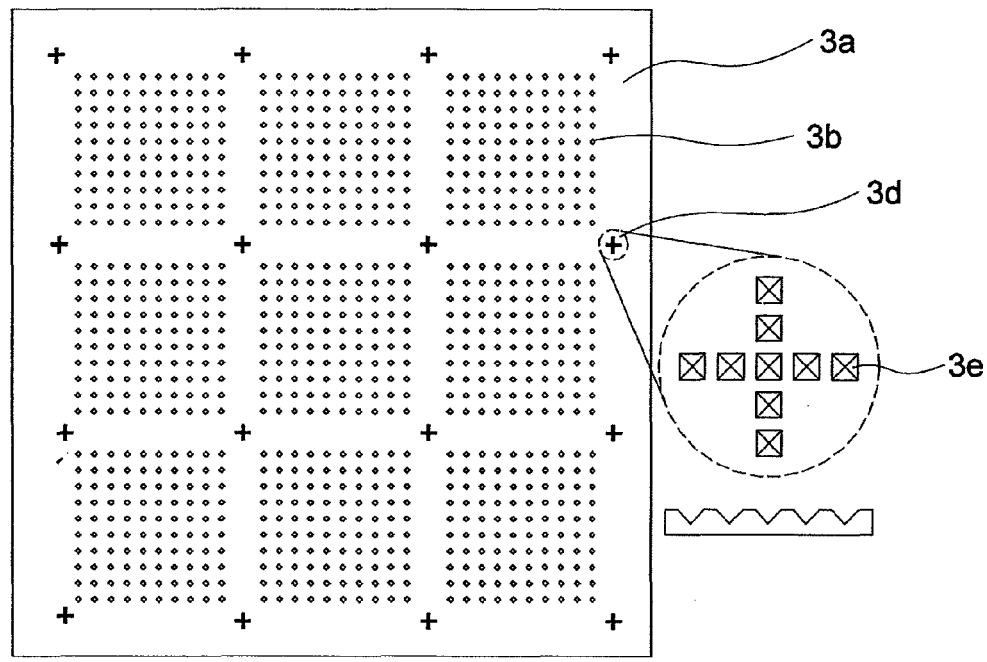
FIG. 3 is a plan view of a microwell array chip 3*a* having a reflective marker 3*d* on a silicon substrate.

FIG. 3 is an implementation Aspect of a reflective marker 3d that is observable by observing scattered light with a fluorescence microscope or fluorescence scanner by forming dips and rises on silicon substrate 3a. It is used as a marker for identifying the positions of clusters of multiple microwells 3b arrayed on silicon substrate 3a. By forming indentation 3e by etching or the like on the substrate and directing a fluorescence excitation beam to an observation device by means of irregular reflection, it is possible to identify the position of the indentation.

Figure 4:
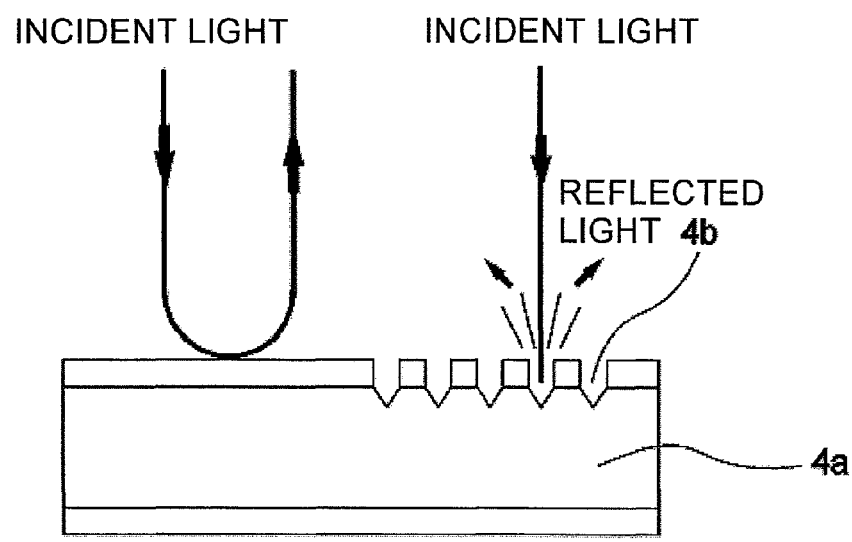
FIG. 4 is a drawing descriptive of the reflective principle of a reflective marker.

FIG. 4 shows the principle involved. For the surface of a substrate 4a without anything, such as the dips or rises shown on the left side of the figure, no excitation light enters the observation device due to full reflection. However, when the indentations on the right side scatter the excitation beam radially, reflected light enters the optical system of the observation device and can be identified.

From the perspective of radially scattering an excitation beam, the bottom of indentation 4b is desirably an inverted pyramid.

Figure 5:
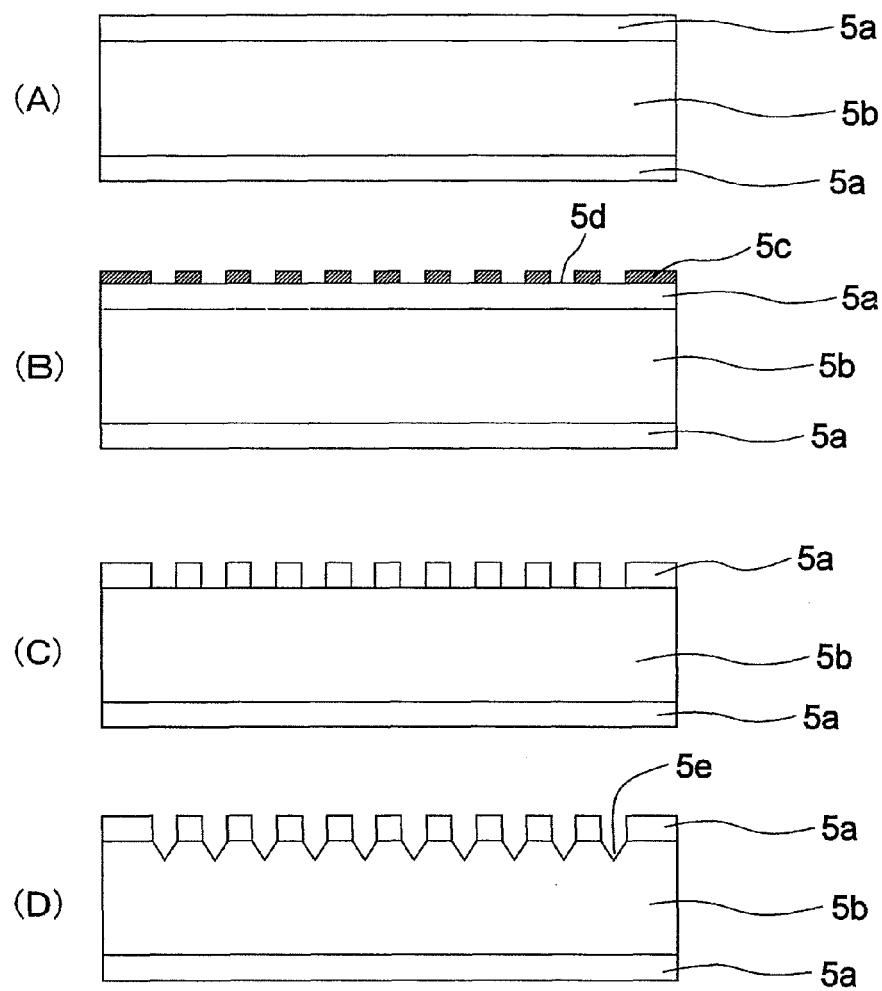
FIG. 5 is a drawing descriptive of (the first half of) the method for manufacturing the microwell array chip of Aspect I of the present invention having a reflective marker in Embodiment 2.
Figure 6:
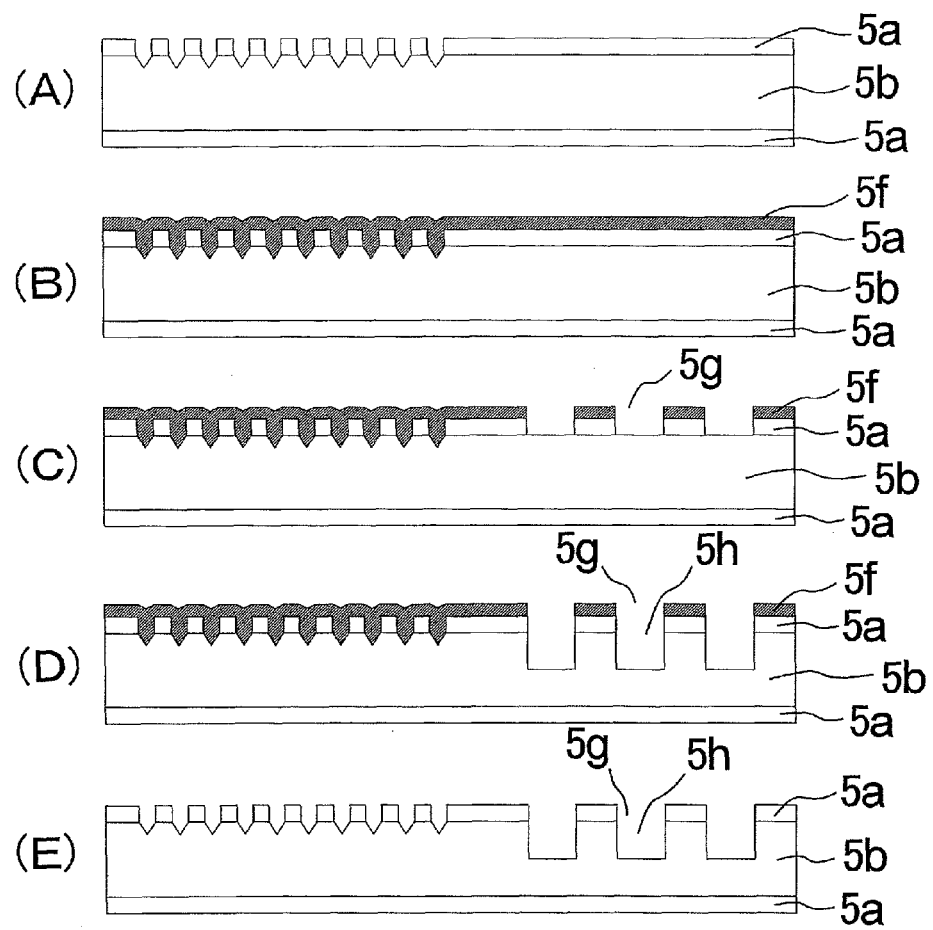
FIG. 6 is a drawing descriptive of (the latter half of) the method for manufacturing the microwell array chip of Aspect I of the present invention having a reflective marker in Embodiment 2.

An example of manufacturing a microwell array chip with reflection markers will be described for the case of a silicon substrate based on FIGS. 5 and 6.

(1) Novolak resin-based positive photoresist OFPR-800 (5c) made by Tokyo Ohka Kogyo (K.K.), for example, is coated on a silicon substrate 5b (FIG. 5(A)) having a silicon oxide film 5a, and a marker pattern 5d is formed on the substrate (FIG. 5(B)).

(2) Hydrofluoric acid is used to remove silicon oxide film 5a having openings from photoresist 5c, exposing the silicon (FIG. 5(C)).

(3) Photoresist 5c is removed, silicon substrate 5b is immersed in an alkali etchant such as tetramethyl ammonium hydroxide or potassium hydroxide to conduct anisotropic etching, forming indentation structure 5e (FIG. 5(D)). At this point, the markers of the present invention are complete. Subsequently, the microwell array structure is fabricated.

(4) As necessary, a thin layer mask of silicon oxide film or silicon nitride film may be again formed on the surface of substrate 5b (FIG. 6(A)).

(5) Photoresist 5f is again applied (FIG. 6(B)) to form a microwell pattern 5g and the silicon oxide film or nitride oxide film of the hole portions is removed with an etchant, exposing the silicon (FIG. 6(C)).

(6) As necessary, photoresist 5f is removed and dry or wet etching is employed to form microwell 5h (FIG. 6(D)).

(7) As necessary, photoresist 5f is removed to obtain a microwell array chip of Aspect I (FIG. 6(E)).

Embodiment 3

A Lip-Structure Embodiment

FIG. 7 shows a microwell structure fabricated based on Aspect II of the present invention.

The present structure can be achieved by selecting an upper thin film of a material that is easy to process with a semiconductor substrate, resin substrate, or the like. The microwells 13 that are formed on the surface of (100) surface silicon substrate 11 measure from several micrometers to several tens of micrometers in both opening diameter and depth. The surface on which no wells are formed is covered with a thin film layer 12' in the form of an oxide film, metal film, or the like. The substrate is etched to form well openings 13a, in which are found eave-shaped protrusions 14 of thin film layer 12'. The thickness of thin film layer 12' is controlled to from several hundred nanometers to several micrometers during formation. Eave-shaped protrusions 14 formed of thin film layer 12' are achieved by an etching method in which thin film layer 12' is etched little during the formation by etching of microwells 13, and etching of the substrate is conducted to the bottom of thin film layer 12'.

In the present embodiment, the manufacturing steps in FIG. 9 will be described using silicon, a typical semiconductor substrate, as an example.

(1) A (100) silicon substrate 11 is hot oxidized to form a thin film layer 12 of roughly several micrometers on the surface (FIG. 9(A)).

(2) A photolithography step is employed to transfer well pattern 15 to silicon substrate 11, exposing silicon in just the well portions (FIG. 9(B)).

(3) The silicon is etched by immersion for several tens of minutes in tetramethyl ammonium hydroxide aqueous solution (90° C., 25 percent). The etching time is determined based on the depth d of the desired well and the size w of the eave (FIG. 8(B)).

(4) After the specified etching time has elapsed, the silicon substrate is removed from the etching solution.

4. The chip was covered with a glass slide to prevent drying out, and the fluorescent intensity was read with a microarray scanner.
5. A total of 4,500 wells on the chip were selected and the number of wells emitting fluorescence was counted. The array rate (fill rate) was calculated by the following equation.

Array rate(fill rate)=(number of wells emitting fluorescence/4,500)×100

TABLE 1

Relation between sample eave and well dimensions and the array (fill) rate

|  | d | p | 2r | W1 | W2 | Array (fill) rate |
|---|---|---|---|---|---|---|
| Sample A | 9.2 micrometers | 13.0 micrometers | 12 micrometers | 0.5 micrometers | 2.7 micrometers | about 73 percent |
| Sample B | 11.8 micrometers | 16.7 micrometers | 13.9 micrometers | 1.4 micrometers | 5.0 micrometers | about 24.9 percent |

The structure of FIG. 9(C) can be formed by the above steps. The tetramethyl ammonium hydroxide aqueous solution employed here permits a hollow structure beneath the oxide film because the oxide film etches slowly and etching progresses in the lateral direction of the wells.

The microwell array chip of Aspect II may also have the structures shown in FIGS. 9(D) and (E). An array chip having microwells of the structures shown in FIGS. 9(D) and (E) can be formed by varying the above method as follows.

For example, when selecting a silicon substrate, the structure of FIG. 9(D) can be achieved by RIE dry etching and suitably selecting a substrate surface orientation and well pattern. For example, face (100), (110), or (111) is selected as the substrate face orientation and a pattern shape that will cause an etching face to appear that is perpendicular to the substrate surface can be selected. The structure of FIG. 9(E) can be achieved by an etching method with isotropic etching characteristics. For example, in common dry etching and etching with a mixed solution of hydrofluoric acid and nitric acid, the silicon etches isotropically, readily yielding the structure of Aspect II of the present invention.

The thin film layer is not limited to an oxide film. A switch to high impurity concentration diffused silicon, germanium, silicon germanium, metal thin films, resins, and the like is also possible. Either wet etching or dry etching may be employed. Since wet etching permits the processing of substrates in batches, it affords good mass production efficiency.

Figure 10:
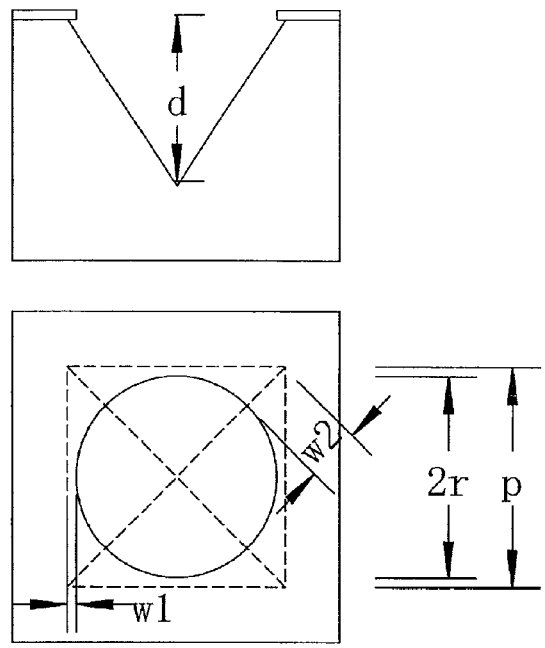
FIG. 10 shows the dimensions of the various components of the microwell array chip produced in Embodiment 3.

An evaluation was made of the microwell array chip array rates (fill rates) when the various dimensions (shown in FIG. 10) of microwell array chips obtained by the above-described method were varied as indicated in Table 1. The results are given in Table 1. The concentration of the cells planted was $10^5$ cells/microliter.

Cell Array Rate (Fill Rate) Evaluation Method
1. Lymphocytes were collected from mice. The concentration of the cells obtained was $10^4$ to $10^5$ cells/microliter. The cells were placed in Hank's balanced salt solution (HBSS) for storage.
2. Each of the cells was fluorescently stained. Each cell was stained with CellTracker Orange, which emitted fluorescence at the excitation wavelength (532 nm) of the fluorescence scanner employed in measurement.
3. The stained cells were planted on the silicon chip with a micropipette. The planting was repeated three times and cells that had not entered wells were finally washed off.

For samples A and B, changes in array (fill) rate based on differences in eave and well dimensions were examined. As a result, it was found that when the cell diameter was 8 micrometers, the array (fill) rate of sample B was worse than that of sample A. This was attributed to the excessively large opening diameter 2r of sample B.

The array (fill) rate increased with the depth of the well, but with a large opening such as that of sample B, the array (fill) rate tended to decrease. Accordingly, the design of the well must suitably take into account the depth, opening diameter, and eave dimension of the well.

Embodiment 4

An Embodiment of Fluorocarbon Film Formation

Figure 11:
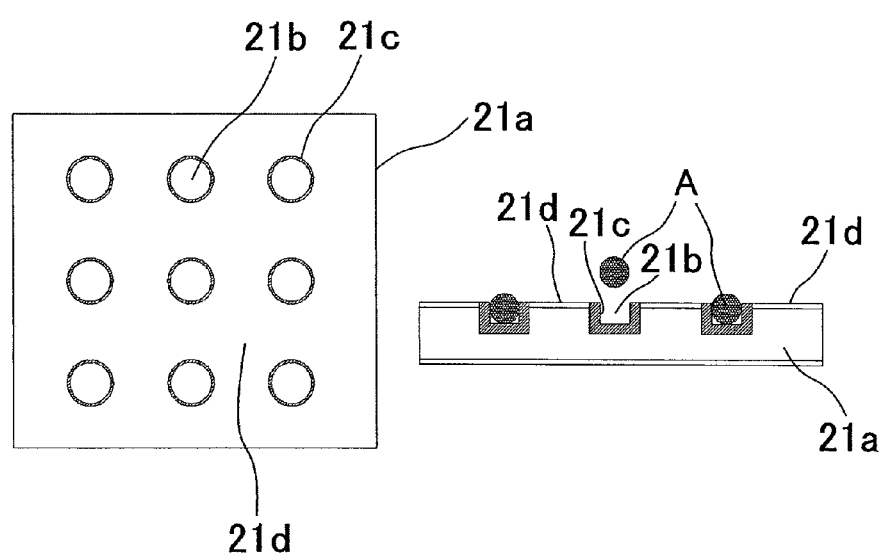
FIG. 11 is a schematic drawing descriptive of a microwell array chip having a fluorocarbon film in the wells.

FIG. 11 is a schematic drawing descriptive of a microwell array chip relating to Aspect III of the present invention.

Multiple microwell patterns 21b are arranged on the surface of silicon substrate 21a. The size of each microwell 21b is from several micrometers to several tens of micrometers. A fluorocarbon film 21c was formed with a CxFy-based gas on the sidewall of each well formed, and a surface energy reducing effect created an inert state. Fluorocarbon film 21c, which exhibited a hydrophobic property, was selectively formed within the microwells, but was not present on the outermost surface 21d of the silicon. The organic cell entering microwell 21b tended not to readily adhere. The effect of providing a fluorocarbon film inside the microwells was particularly marked when the microwell was deep.

Figure 12:
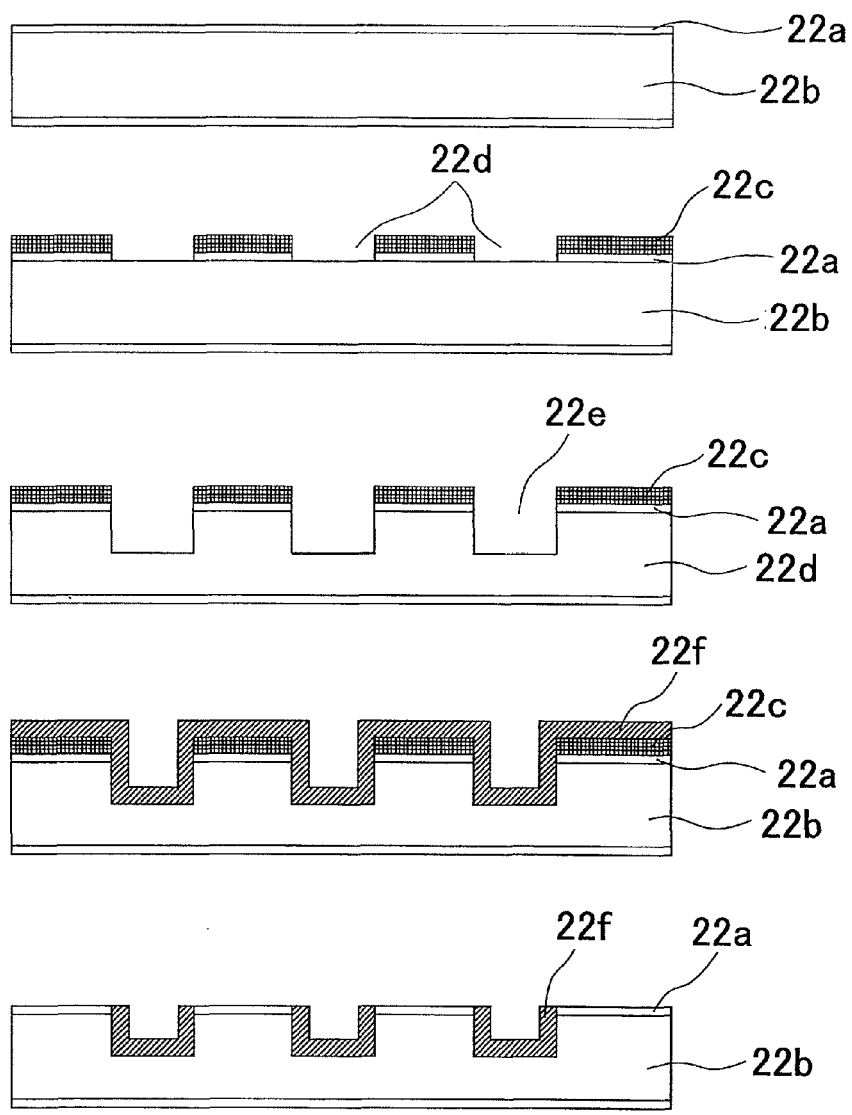
FIG. 12 is a drawing descriptive of the method for manufacturing a microwell array chip having a fluorocarbon film in the wells of Embodiment 4.

FIG. 12 shows the steps of manufacturing a microwell array chip employing a silicon substrate.

(1) Novolak resin-based positive photoresist OFPR-800 (22c) made by Tokyo Ohka Kogyo (K.K.), for example, is coated on a silicon substrate 22b having a silicon oxide film 22a, and a microwell pattern 22d is formed. At this time, heat treatment following development is conducted at a lower temperature (from about 100 to 110° C.) than usual.

(2) Silicon substrate 22b is etched by introducing a silicon etching gas such as SF6 into a plasma dry etching device to form microwells 22e.

(3) A CxFy-based gas is introduced into the same etching device to conduct plasma film formation. At this point, a fluorocarbon film 22f forms inside the wells and on the silicon substrate surface. This step can also be conducted by conveying the substrate into a plasma CVD device and conducting the same processing.

(4) The substrate removed from the device is immersed in an organic solvent such as methanol or acetone to remove the photoresist. At this time, the fluorocarbon film formed on the resist is also lifted off.

(5) A microwell array chip is obtained in which the outermost surface of the silicon substrate is coated with a silicon oxide film 22a and the interior of the wells is coated with an inert fluorocarbon film 22f.

The array (fill) rate of a microwell array chip obtained by the above-described method was evaluated by the same method as in Embodiment 3. The collection rate was evaluated by the following method. The results are given in Table 2. Table 2 gives the evaluation results for a microwell array chip in which a fluorocarbon film was formed within the wells. The same well diameter and depth were selected for all of the samples. The concentration of the planted cells was $10^5$ cells/microliter.

Collection Rate Evaluation Method
1. Based on the above-described cell array rate evaluation method, cells were planted in a microwell array.
2. A random number of wells (about 10 to 30) were selected and the cells were removed from the wells with a micromanipulator. At that time, the removal was not conducted aggressively; caution was exercised to employ the same removal conditions for each well.
3. For the randomly selected number of wells, the ratio of the number of wells from which cells were successfully removed was denoted as the collection rate.

Collection rate=(number of wells from which cells successfully removed)/number of wells randomly selected)×100

TABLE 2

| | Sample | | | | | |
|---|---|---|---|---|---|---|
| | A | B | C | D | E | F |
| Array (fill) rate | 99.4% | 99.2% | 99.2% | 99.4% | 99.3% | 98.9% |
| Collection rate | 0% | 10% | 6.7% | 50% | 30% | 89.3% |

Sample specifications: Well diameter: 11 micrometers, depth 30 micrometers
Samples A-C: No coating, etching time: 8 minutes
Samples D-F: Coating present, etching time: 8 minutes+coating time: 1 minute Embodiment 5

Figure 13:
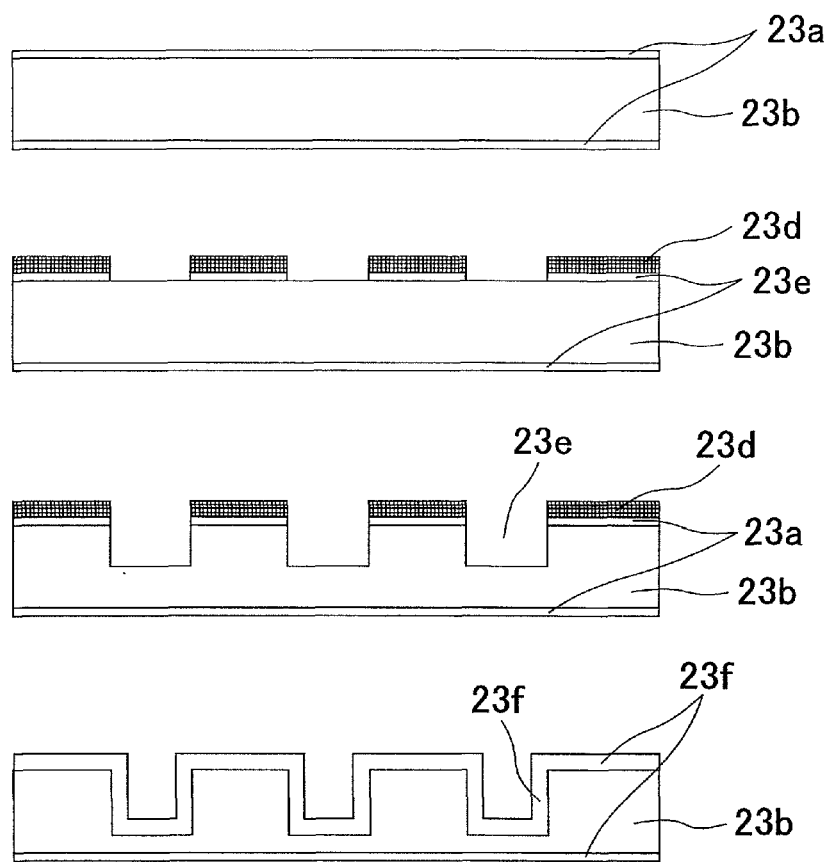
FIG. 13 is a drawing descriptive of the method for manufacturing a microwell array chip having an oxide film (silicon oxide) in the wells of Embodiment 5.

Manufacturing a Microwell Array Chip Having an Oxide Film (Silicon Oxide) in the Wells (See FIG. 13)

(1) Novolak resin-based positive photoresist OFPR-800 made by Tokyo Ohka Kogyo (K.K.), for example, is coated on a silicon substrate 23b having a silicon oxide film 23a, and a microwell pattern 23d is formed.

(2) A silicon etching gas such as SF6 is introduced into a plasma dry etching device to etch silicon substrate 23b and form microwells 23e.

(3) The photoresist on the substrate that has been removed from the device is removed with a resist separating solution such as a mixed solution of sulfuric acid and hydrogen peroxide water.

(4) The substrate is ammonia washed (ammonia+hydrogen peroxide water+water) with an RCA wash and hydrochloric acid washed (hydrochloric acid+hydrogen peroxide water+water).

(5) The substrate is introduced into a heat treatment furnace in a dry oxygen atmosphere and hot oxide treated for 30 minutes at 1,100° C.

(6) After the temperature drops, the substrate is removed from the heat treatment furnace.

(7) This yields a microwell array chip with an oxide film 23f formed on the silicon substrate surface and in the wells and an oxide film (silicon oxide) formed in the wells.

The array (fill) rate and collection rate of the microwell array chip obtained by the above-described method were evaluated by the same methods as set forth above. The results are given in Table 3. The same well diameter and depth were selected for all of the samples. The concentration of cells planted was $10^5$ cells/microliter.

TABLE 3

| | Sample | | | | | |
|---|---|---|---|---|---|---|
| | A | B | C | D | E | F |
| Array (fill) rate | 99.4% | 99.2% | 99.2% | 91.6% | 98.4% | 98.5% |
| Collection rate | 0% | 10% | 6.7% | 45% | 30% | 55.6% |

Sample specifications: Well diameter: 11 micrometers, depth 30 micrometers
Samples A-C: No oxide film, etching time: 8 minutes
Samples D-F: Oxide film present. Etching time: 8 minutes, Oxidation temperature: 1,100° C., Oxidation atmosphere: Dry oxygen, Oxidation time: 30 minutes, Oxidation film thickness: 63 nm (on silicon crystal face (100))

Embodiment 6

Smoothness Treatment

Figure 17:
FIG. 17 is an enlarged photograph of a microwell the inner wall of which has been treated for smoothness in Embodiment 6.

In the manufacturing of Embodiment 4, the inner walls of the microwell array chip were treated for smoothness prior to formation of the fluorocarbon film. The smoothness treatment was conducted using a Multiplex ASE etching device made by STS Corporation and adjusting the process cycle times of the etching step and protective film formation step. In this manner, two types of microwell array chips were manufactured: one having dips and rises 0.5 micrometer in height on the inner walls, and the other having dips and rises 0.1 micrometer in height on the inner walls. FIG. 17 is an enlarged photograph of microwells having dips and rises 0.1 micrometer in height on the inner walls.

The collection rate of the microwell array chip obtained by the above-described method was evaluated by the same method as above. The results are given in Table 4. The concentration of cells planted was $10^5$ cell/microliter. Immediately following planting, there was no great difference in the collection rates of the two chips. However, when an hour had elapsed following planting, the collection rate of the chip provided with dips and rises 0.5 micrometer in height through a smoothing treatment dropped to 0 percent, while the chip provided with dips and rises 0.1 micrometer in height through a smoothing treatment more or less maintained the collection rate it had immediately after planting. This indicated that the smaller the height of the dips and rises on the inner walls, the greater the prevention of adhesion of cells to the wells with the passage of time. Further, smoothing of the inner walls was thought to allow the coating of Embodiment 4 to function efficiently.

TABLE 4

|  | Dip and rise height 0.5 micrometer | Dip and rise height 0.1 micrometer |
|---|---|---|
| Collection rate immediately following planting | 80% | 100% |
| Collection rate one hour after planting | 0% | 90% |

Embodiment 7

Formation of Protrusions in Openings

Figure 18:
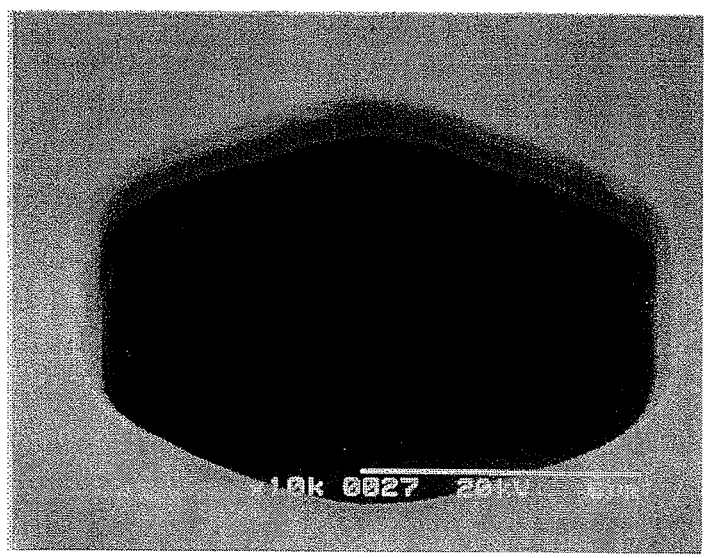
FIG. 18 is an enlarged photograph of a microwell in the opening of which is formed a protrusion in Embodiment 7.

In the manufacturing of Embodiment 4, protrusions 0.6 micrometer in height were formed in the openings of the microwells. Using a Multiplex ASE etching device made by STS Corporation, the process cycle time of the device was extended during initial etching to form protrusions of desired height. Following the formation of protrusions, the process cycle time was adjusted to manufacture microwells having protrusions only in the openings. FIG. 18 is an enlarged photograph of microwells in which protrusions have been formed in the openings.

Following manufacturing of the microwells, it is possible to form a fluorocarbon film on the inner walls. Protrusions can be formed at any position. The process cycle time can be adjusted at a position where the formation of a protrusion is desired to make a protrusion in the middle of the well, on the bottom of the well, or anywhere else. Suitable selection of the shape and number of protrusions can be anticipated to yield a variety of effects.

INDUSTRIAL APPLICABILITY

In the microwell array chip of Aspect I of the present invention, markers in the form of a fluorescent substance, reflective structures, or the like are present at targeted locations. These markers function to identify positions, thereby facilitating the identification of positions by fluorescence microscope. In the microwell array chip of Aspect I, microwell positions can be readily determined by fluorescence microscope, image scanner, or the like. As a result, a single specific specimen of an organic cell stored in an individual microwell—for example, an antigen-specific lymphocyte—can be readily specified. As a result, it is possible to remove an antigen-specific lymphocyte that has been detected and clone the antigen-specific antibody gene or T cell receptor gene. For example, once it is possible to clone an antigen-specific antibody gene, it can be used to produce large quantities of human monoclonal antibody. It is thought that by administering this antibody to a human patient with an infectious disease, it is possible to treat and prevent the infectious disease. Further, by using the microwell array chip of Aspect I, it is also possible to distinguish blood cells. That is, by setting the microwells to a prescribed diameter, it is possible to separate blood cells into those exceeding and those falling below the microwell diameter.

Based on Aspect II of the present invention, since a cell that has entered a well catches on the protrusion (eave) at the top of the well, it can be retained in the well with high probability and not flow to the exterior of the well during washing. For example, when the well has an inverted pyramid structure, the formation of a lip changes the distribution of fluid on the chip surface and within the well. Thus, a cell that has already entered can be prevented from flowing out with the liquid during washing. Still further, even when a cell that has entered a well begins to move toward the exterior of the well, it catches on the eave and tends to remain within the well.

Further, when removing a cell that has entered a well, careful design of the shape of the well can prevent the generation of a vacuum between the cell and the well surface during suction. That is, when the well is imparted with the shape of an inverted pyramid, the ridgelines function to relieve pressure so that during aspiration of the cell, no vacuum forms between the well and the cell, permitting ready collection of the cell.

In the microwell array chip of Aspect III of the present invention, each microwell can contain just one specimen organic cell, such as a lymphocyte. Thus, for example, it is possible to specify antigen-specific lymphocytes at the individual cell level. That is, by using the microwell array chip of Aspect III in the detection of antigen-specific lymphocytes, since only one specimen lymphocyte is contained in a given microwell, it is possible to specify a single cell in the form of a specimen lymphocyte reacting with the antigen.

As a result, for example, an antigen-specific lymphocyte that has been detected can be removed and the antigen-specific antibody gene or T cell receptor gene can be cloned. For example, once it is possible to clone the antigen-specific antibody gene, it can be used to produce large amounts of human monoclonal antibody. It is thought that this antibody can then be administered to patients with an infectious disease or the like to treat and prevent the infectious disease or the like.

The invention claimed is:

1. A method of recovering a single specimen organic cell, which comprises:
   storing a single specimen organic cell in each microwell of a microwell array chip made of silicon and comprising multiple microwells; and
   individually recovering a stored single specimen organic cell from the microwell,
   wherein each microwell is of a size and shape holding just one organic cell,
   wherein the surface of said microwell array is covered by a film of silicon oxide,
   wherein the inner surface of said microwells is coated with a fluorocarbon film, so that the interior surface of said microwells prevents adhesion of the organic cell and facilitates recovery of the stored organic cell from the microwell, and
   wherein said single specimen organic cell is an antigen-specific B lymphocyte reacting to a specific antigen.

2. The method of recovering a single specimen organic cell according to claim 1, wherein said method further comprises detecting said antigen-specific B lymphocyte before the recovering step.

3. The method of recovering a single specimen organic cell according to claim 1, wherein the shape of each of said microwells is cylindrical, polyhedral, comprised of multiple surfaces, inversely conical, inversely pyramidal, or a combination of two or more of the above.

4. The method of recovering a single specimen organic cell according to claim 1, wherein a diameter of a largest circle that can be inscribed within a planar shape of the microwell of the microwell array chip falls within a range of from 0.5 to 2-fold of a diameter of an organic cell that is in the microwell, and the depth of the microwell falls within a range of from 0.5 to 4-fold of the diameter of the organic cell that is contained in the microwell.

5. The method of recovering a single specimen organic cell according to claim 1, wherein said microwell array chip further comprises a hydrophobic region surrounding said multiple microwells.

6. The method of recovering a single specimen organic cell according to claim 5, wherein said hydrophobic region has a silicon surface or fluorine-containing surface.

* * * * *